United States Patent
Rabinovich et al.

(10) Patent No.: US 10,017,782 B2
(45) Date of Patent: Jul. 10, 2018

(54) IMMUNE CELLS MODIFIED BY TRANSIENT TRANSFECTION OF RNA

(71) Applicant: Yale University, New Haven, CT (US)

(72) Inventors: Peter M. Rabinovich, Madison, CT (US); Sherman M. Weissman, New Haven, CT (US); Erkut Bahceci, Hamden, CT (US); Marina E. Komarovskaya, Milford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/012,285

(22) Filed: Feb. 1, 2016

(65) Prior Publication Data

US 2016/0230188 A1 Aug. 11, 2016

Related U.S. Application Data

(63) Continuation of application No. 13/019,829, filed on Feb. 2, 2011, now Pat. No. 9,249,423, which is a continuation-in-part of application No. 12/025,700, filed on Feb. 4, 2008, now Pat. No. 8,859,229.

(60) Provisional application No. 60/899,144, filed on Feb. 2, 2007.

(51) Int. Cl.

| | |
|---|---|
| *A61K 9/66* | (2006.01) |
| *C12N 15/85* | (2006.01) |
| *A61K 48/00* | (2006.01) |
| *C12N 5/074* | (2010.01) |
| *A61K 35/17* | (2015.01) |
| *A61K 35/33* | (2015.01) |
| *A61K 35/36* | (2015.01) |
| *A61K 35/12* | (2015.01) |

(52) U.S. Cl.
CPC .............. *C12N 15/85* (2013.01); *A61K 35/17* (2013.01); *A61K 35/33* (2013.01); *A61K 35/36* (2013.01); *A61K 48/005* (2013.01); *C12N 5/0696* (2013.01); *A61K 2035/124* (2013.01); *C12N 2501/602* (2013.01); *C12N 2501/603* (2013.01); *C12N 2501/604* (2013.01); *C12N 2501/606* (2013.01); *C12N 2506/094* (2013.01); *C12N 2506/1307* (2013.01); *C12N 2510/00* (2013.01)

(58) Field of Classification Search
CPC .............................. C12N 15/85; A61K 48/005
USPC .......................................................... 424/455
See application file for complete search history.

(56) References Cited

U.S. PATENT DOCUMENTS

| | | |
|---|---|---|
| 4,394,448 A | 7/1983 | Szoka |
| 4,619,794 A | 10/1986 | Hauser |
| 4,946,778 A | 8/1990 | Ladner |
| 5,091,513 A | 2/1992 | Huston |
| 5,250,431 A | 10/1993 | Rudd |
| 5,256,555 A | 10/1993 | Milburn |
| 5,359,046 A | 10/1994 | Capon |
| 5,686,281 A | 11/1997 | Roberts |
| 5,712,149 A | 1/1998 | Roberts |
| 5,747,292 A | 5/1998 | Greenberg |
| 5,807,707 A | 9/1998 | Andrews |
| 5,837,693 A | 11/1998 | German |
| 5,840,304 A | 11/1998 | Davis |
| 5,858,740 A | 1/1999 | Finer |
| 5,861,314 A | 1/1999 | Philip |
| 5,912,172 A | 6/1999 | Eshhar |
| 6,103,521 A | 8/2000 | Capon |
| 6,355,476 B1 | 3/2002 | Kwon |
| 6,407,221 B1 | 6/2002 | Capon |
| 6,410,319 B1 | 6/2002 | Raubitschek |
| 6,825,325 B1 | 11/2004 | Fischer |
| 7,049,136 B2 | 5/2006 | Seed |
| 7,070,995 B2 | 7/2006 | Jensen |
| 7,323,553 B2 | 1/2008 | Fahrner |
| 7,435,596 B2 | 10/2008 | Campana |
| 7,446,179 B2 | 11/2008 | Jensen |
| 7,466,179 B2 | 12/2008 | Huang |
| 7,514,537 B2 | 4/2009 | Jensen |

(Continued)

FOREIGN PATENT DOCUMENTS

| | | |
|---|---|---|
| WO | 9914346 | 3/1999 |
| WO | 0014257 | 3/2000 |
| WO | 0018958 | 4/2000 |
| WO | 2004065546 | 8/2004 |
| WO | 2005044996 | 5/2005 |
| WO | 2006052534 | 5/2006 |
| WO | 2008095141 | 8/2008 |
| WO | 2009077134 | 6/2009 |
| WO | 2009091826 | 7/2009 |

OTHER PUBLICATIONS

Cooper (2003, Blood, 101:1637-1644).*

(Continued)

*Primary Examiner* — Valarie E Bertoglio
(74) *Attorney, Agent, or Firm* — Pabst Patent Group LLP

(57) ABSTRACT

RNA prepared by in vitro transcription using a polymerase chain reaction (PCR)-generated template can be introduced into a cell to modulate cell activity. This method is useful in de-differentiating somatic cells to pluripotent, multipotent, or unipotent cells; re-differentiating stem cells into differentiated cells; or reprogramming of somatic cells to modulate cell activities such as metabolism. Cells can also be transfected with inhibitory RNAs, such as small interfering RNA (siRNA) or micro RNA (miRNA), or combinations thereof to induce reprogramming of somatic cells. For example, target cells are isolated from a donor, contacted with one or more RNA's causing the cells to be de-differentiated, re-differentiated, or reprogrammed in vitro, and administered to a patient in need thereof. The resulting cells are useful for treating one or more symptoms of a variety of diseases and disorders, for organ regeneration, and for restoration of the immune system.

12 Claims, 14 Drawing Sheets

(56) References Cited

U.S. PATENT DOCUMENTS

| | | |
|---|---|---|
| 8,026,097 B2 | 9/2011 | Campana |
| 8,071,374 B2 | 12/2011 | Har-Noy |
| 8,399,645 B2 | 3/2013 | Campana |
| 8,859,229 B2 | 10/2014 | Rabinovich |
| 9,249,423 B2 | 2/2016 | Rabinovich |
| 9,605,049 B2 | 3/2017 | Campana |
| 2002/0001841 A1 | 1/2002 | Kaltoft |
| 2002/0018749 A1 | 2/2002 | Hudson |
| 2003/0083272 A1 | 5/2003 | Wiederholt |
| 2003/0087846 A1 | 5/2003 | Wolpert |
| 2003/0148982 A1 | 8/2003 | Brenner |
| 2004/0038886 A1 | 2/2004 | Finney |
| 2004/0043401 A1 | 3/2004 | Sadelain |
| 2004/0058445 A1 | 3/2004 | Ledbetter |
| 2005/0113564 A1 | 5/2005 | Campana |
| 2006/0029595 A1 | 2/2006 | Kwon |
| 2006/0078994 A1 | 4/2006 | Healey |
| 2006/0127985 A1 | 6/2006 | Goodwin |
| 2006/0188490 A1 | 8/2006 | Hoerr |
| 2008/0152586 A1 | 6/2008 | Hudson |
| 2008/0260706 A1 | 10/2008 | Rabinovich |
| 2008/0311076 A1 | 12/2008 | Spencer |
| 2009/0136498 A1 | 5/2009 | Haurum |
| 2009/0191172 A1 | 7/2009 | Cooper |
| 2009/0196877 A1 | 8/2009 | Chen |
| 2009/0226404 A1 | 9/2009 | Schuler |
| 2009/0257991 A1 | 10/2009 | Li |
| 2009/0263421 A1 | 10/2009 | Spetz-Holmgren |
| 2011/0038836 A1 | 2/2011 | Cooper |
| 2011/0044939 A1 | 2/2011 | Feuerer |
| 2011/0059056 A1 | 3/2011 | Grawunder |
| 2011/0070219 A1 | 3/2011 | Seefeldt |
| 2011/0091936 A1 | 4/2011 | Gawlitzek |
| 2011/0104128 A1 | 5/2011 | Cooper |
| 2011/0110909 A1 | 5/2011 | Ildstad |
| 2011/0143436 A1 | 6/2011 | Dahl |
| 2011/0287979 A1 | 11/2011 | Gurney |
| 2011/0300179 A1 | 12/2011 | Spetz-Holmgren |
| 2012/0015434 A1 | 1/2012 | Campana |
| 2012/0134970 A1 | 5/2012 | Yang |
| 2013/0071414 A1 | 3/2013 | Dotti |
| 2013/0216509 A1 | 8/2013 | Campana |
| 2013/0266551 A1 | 10/2013 | Campana |
| 2014/0050709 A1 | 2/2014 | Leen |
| 2014/0328812 A1 | 11/2014 | Campana |
| 2014/0341869 A1 | 11/2014 | Campana |
| 2015/0017120 A1 | 1/2015 | Wittrup |
| 2015/0283178 A1 | 10/2015 | June |
| 2015/0290244 A1 | 10/2015 | June |
| 2016/0009784 A1 | 1/2016 | Campana |
| 2016/0151491 A1 | 6/2016 | Rabinovich |
| 2016/0230188 A1 | 8/2016 | Rabinovich |

OTHER PUBLICATIONS

Loskog (2006, Leukemia, 20:1819-1828).*
Arnaud-Barbe, "Transcription of RNA templates by T7 RNA polymerase", Nuc. Acids Res., 26(15):3550-3554 (1998).
Bahceci, "Immunotherapy of B cell malignancies using transiently redirected cytotoxic T cells", Blood, 110(11)Part 1:808A (2007).
Barbour, et al., The nucleotide sequence of a linear plasmid of borrelia burgdorferi reveals similarities to those of circular plasmids of other prokaryotes , J Bacteriology, 178(22):6635-9 (1995).
Boczkowski, "Induction of tumor immunity and cytotoxic T lymphocyte responses using dendritic cells transfected with messenger RNA amplified from tumor cells", Cancer Res., 60(4):1028-1034 (2001).
Buganim, et al., Single-cell gene expression analysis of cellular reprograming reveal a stochastic early and hierarchic late phase , Cell, 150:1209-22 (2012).
Chamberlin, "New RNA polymerase from *Escherichia coli* infected with bacteriophage T7", Nature, 228(5268):227-231 (1970).
Chan, et al., The kalilo linear senescence-inducing plasmid of neurospora is an invertron and encodes DNA and RNA polymerases , 20 Current Genetics, 225-37 (1991).
Cheung, "Anti-idiotypic antibody facilitates scFv chimeric immune receptor gene transduction and clonal expansion of human lymphocytes for tumor therapy", Hybridoma and Hybridomics, 22(4):209-218 (2003).
Collas, et al., On the way to reprograming cells to pluripotency using cell-free extracts , Reprod Biomed 762-770 (2006).
Cougot, "Cap-tabolism", Trends in Biochem. Sci., 29(8):436-444 (2004).
Davanloo, "Cloning and expression of the gene for bacteriophage T7 RNA polymerase", Proc. Natl. Acad. Sci. USA, 81(7):2035-2039 (1984).
Djuris and Ellisx, Epigenetics of induced pluripotency, the seven headed dragon , Stem Cell Res Ther, 1:3 1-6 (2010).
Dunn and Studier, "Complete nucleotide sequence of bacteriophage T7 DNA and the locations of T7 genetic elements", J. Mol. Biol., 166(4):477-535 (1983).
Elango, "Optimized transfection of mRNA transcribed from a d(A/T)100 tail-containing vector", Biochem. Biophys. Res. Comm., 330(3), 958-966 (2005).
Felgner and Ringold, "Cationic liposome-mediated transfection", Nature, 337(6205):387-388 (1989).
Fuke and Ohno, Role of poly (A) tail as an identity element for mRNA nuclear export , Nucl Acids Res., 36:1037-49 (2008).
Hanna, et al., Direct reprograming of terminally differentiated mature B lymphocytes pluripotency , Cell, 133:250-64 (2008).
Holtkamp, "Modification of antigen-encoding RNA increases stability, translational efficacy, and T-cell stimulatory capacity of dendritic cells", Blood, 108(13):4009-4017 (2006).
Imai, "Chimeric receptors with 4-1BB signaling capacity provoke potent cytotoxicity against acute lymphoblastic leukemia", Leukemia,18(4):676-684 (2004).
Imai, "Genetic modification of primary natural killer cells overcomes inhibitory signals and induces specific killing of leukemic cells", Blood, 106(1):376-383 (2005).
Karlock, et al., Mutations in the yeast mitochondrial RNA polymerase specificity factor, Mtf1, verify an essential role in promoter utilization , J Biol Chem., 277(31):28143-9 (2002).
Kiyama and Oishi, "In transcription of a poly(dA) × poly(dT)-containing sequence is inhibited by interaction between the template and its transcripts", Nucleic Acids Res., 24(22):4577-4583 (1996).
Kiyama, "Instability of plasmid DNA maintenance caused by transcription of poly (dT)-containing sequences in *Escherichia coli*", Gene, 150(1):57-61 (1994).
Kotani, "Improved methods of retroviral vector transduction and production for gene therapy", Hum. Gene Ther., 5(1):19-28 (1994).
Kowolik, "CD28 costimulation provided through a CD19-specific chimeric antigen receptor enhances in vivo persistence and antitumor efficacy of adoptively transferred T cells", Cancer Res., 66(22)10995-11004 (2006).
Le Dantrec, et al., Genomic sequence and transcriptional analysis of a 23-kilobase mycobacterial linear plasmid: Evidence for horizontal transfer and identification of plasmid maintenance systems , J Bacteriology, 183(7):2157-64 (2001).
Lee, "Efficient autointegration of avian retrovirus DNA in vitro", J. Virol., 64(12):5958-5965 (1990).
Liu, "Development and validation of a T7 based linear amplification for genomic DNA", BMC Genomics, 4(1):19 (2003).
MacDonald, "Termination and slippage by bacteriophage T7 RNA polymerase", J. Mol. Biol., 232(4):1030-1047 (1993).
Mackett, "General method for production and selection of infectious vaccinia virus recombinants expressing foreign genes", J. Virol., 49(3):857-864 (1984).
Maherali, et al., Guideline and techniques for the generation of induced pluripotent stem cells , Stem Cell, 3:596-605 (2008).
Mielke, et al., Stabilized long-term expression of heterodimeric proteins from tricistronic mRNA , Gene, 254:1-6 (2000).
Mochizuki, et al., The large linear plasmid pSLA2-L of Streptomyces rochei has an unusually condensed gene organization for secondary metabolism , Mole Microbiol., 48(6):1501-10 (2003).

(56) References Cited

OTHER PUBLICATIONS

Muhlrad and Parker, Aberrant mRNAs with extended 3 UTRa are substrates for rapid degradation by mRNA surveillance ,RNA,5:1299-307 (1999).
Nacheva and Berzal-Herranz, "Preventing nondesired RNA-primed RNA extension catalyzed by T7 RNA polymerase", Eur. J. Biochem., 270(7):1458-1465 (2003).
Nair, et al., "Induction of primary carcinoembryonic antigen (CEA)-specific cytoxic T lymphocytes in vitro using human dendritic cells transfected with RNA", Nature Biotechnology, 16(4):364-369 (1998).
Nakano, "Efficient coupled transcription/translation from PCR template by a hollow-fiber membrane bioreactor", Biotechnol. Bioeng., 64(2):194-199 (1999).
Nienhuls, et al, Genotoxicity of Retroviral integration in hematopoietic cells , Mole Therapy, 13:1031-49 (2006).
Nishikawa, "Nonviral vectors in the new millennium: delivery barriers in gene transfer", Hum. Gene Ther., 12(8):861-870 (2001).
Pestova, "Molecular mechanisms of translation initiation in eukaryotes", Proc. Natl. Acad. Sci., 98(13):7029-7036 (2001).
Plath and Lowry, et al., Progress in understanding reprograming to induced pluripotent state , Nature Reviews, 12:253-65 (2011).
Rabinovich, "Synthetic messenger RNA as a tool for gene therapy", Human Gene Therapy, 17(10):1027-1035 (2006).
Saeboe-Larssen, "mRNA-based electrotransfection of human dendritic cells and induction of cytotoxic T lymphocyte responses against the telomerase catalytic subunit (hTERT)", J. Imm. Methods, 259(1-2):191-203 (2002).
Saltzman and Desai, "Drug delivery in the BME curricula", Annals of Biomedical Engineering, 34(2):270-275 (2006).
Santopiatro, et al., Cloning and nucleotide sequence of a linear DNA plasmid from xanthophyfiomyces dendrorhous (pfaffia rhodozyma) , Folia Microbiol., 46(4):277-88 (2001).
Sasaki, et al., "Translation initiation at the CUU codon is mediated by the internal ribosome entry site of an insect picorna-like virus in vitro", J. of Virology, 73:129-1226 (1999).
Schenborn and Mierendorf, "A novel transcription property of SP6 and T7 RNA polymerases: dependence on template structure", Nuc Acids Res., 13(17):6223-6236 (1985).
Schultze, "Follicular lymphomas can be induced to present alloantigen efficiently: a conceptual model to improve their tumor immunogenicity", Proc. Natl. Acad. Sci., 92(18):8200-8204 (1995).
Shiramizu, "Identification of a common clonal human immunodeficiency virus integration site in human immunodeficiency virus-associated lymphomas", Cancer Res., 54(8):2069-2072 (1994).
Spratt, "The lognormal frequency distribution and human cancer", J. Surgical Research, 9(3):151-157 (1969).
Stadtfeld, et al., Defining molecular cornerstones during fibroblast to iPS cell reprograming in mouse , Cell Stem Cell, 2:230-40 (2008).
Stepinski, "Synthesis and properties of mRNAs containing the novel "anti-reverse" cap analogs 7-methyl(3'-O-methyl)GpppG and 7-methyl (3'-deoxy)GpppG", RNA, 7(10):1486-1495 (2001).
Sullivan, et al., Elucidating nuclear reprogramming mechanisms: taking a synergistic approach , Reprod Biomed. Online, 165(1);41-50 (2008).
Takahashi, et al., Induction of pluripotent stem cells from mouse embryonic and adult fibroblast cultures by defined factors , Cell, 128:663-76 (2006).
Triana-Alonso, "Self-coded 3'-extension of run-off transcripts produces aberrant products during in vitro transcription with T7 RNA polymerase", J. Biol. Chem., 270(11):6298-6307 (1995).
Verma and Somia, "Gene therapy—promises, problems and prospects", Nature, 389(6648):239-242 (1997).
Vlachakis, et al., "Meis3 synergizes with Pbx4 and Hoxb1b in promoting hindbrain fates in the zebrafish",Development, 128:1299-1312 (2001).
Wahie, Poly (A) tail length control is caused by termination of progressive synthesis , J Biol Chem., 270:2800-8 (1995).
Warren, et al., "Highly efficient reprogramming to pluripotency and directed differentiation of human cells with synthetic modified mRNA", Cell Stem Cell, 7:618-30 (2010).
Wolff, "Direct gene transfer into mouse muscle in vivo", Science, 247(4949 Pt 1):1465-1468 (1990).
Yakubov, et al., Reprogramming of human fibroblasts to pluripotent stem cells using mRNA of four transcription factors , Biochem Biophys Res., 394:189-9 (2010).
Yamanaka, "Induction of pluripotent stem cells from mouse fibroblasts by four transcription factors", Cell Prolif., 41(Suppl 1):51-56 (2008).
Yu, "Induced pluripotent stem cell lines derived from human somatic cells", Science, 318(5858):1917-1920 (2007).
Yu, "Structural and functional analysis of an mRNP complex that mediates the high stability of human beta-globin mRNA", Molecular and Cellular Biology, 21(17):5879-5888 (2001).
Ahuja, et al., "Depletion of B cells in murine lupus: efficacy and resistance", J Immunology, 179:3351-3361 (2007).
Barber, et al., "Chimeric NKG2D receptor-expressing T cells as an immunotherapy for multiple myeloma", Exp Hematol., 36:1318-28 (2008).
Barrett, et al., "Chimeric antigen receptor therapy for cancer.", Annu Rev Med., 65:333-47 (2014).
Barrett, et al., "Regimen-specific effects of RNA-modified chimeric antigen receptor T cells in mice with advanced leukemia", Hum Gene Ther., 24:717-27 (2013).
Barry, et al., "Granzyme B short-circuits the need for caspase 8 activity during granule-mediated cytotoxic T-lymphocyte killing by directly cleaving Bid", Mol Cell Biol., 20:3781-94 (2000).
Beatty, et al., "Mesothelin-specific chimeric antigen receptor mRNA-engineered T cells induce anti-tumor activity in solid malignancies", Cancer Immunol Res., 2:12-120 (2014).
Begley, et al., "Immunosensitization with a Bcl-2 small molecule inhibitor", Cancer Immunol Immunother, 58:699-708 (2009).
Berger, et al., "Analysis of transgene-specific immune responses that limit the in vivo persistence of adoptively transferred HSV-TK-modified donor T cells after allogeneic hematopoietic cell transplantation", Blood, 107:2294-302 (2006).
Biagi, et al., "Chimeric T-cell receptors: New challenges for targeted immunotherapy in hematologic malignancies", Haematologica, 92:381-88 (2007).
Bonini, et al., "HSV-TK gene transfer into donor lymphocytes for control of allogeneic graft-versus-leukemia", Science, 276:1719-24 (1997).
Brawerman, et al,, "The role of the poly(A) sequence in mammalian messenger RNA", Crit Rev Biochem., 10:1-38 (1981).
Brentjens, et al., "CD19-targeted T cells rapidly induce molecular remissions in adults with chemotherapy-refractory acute lymphoblastic leukemia", Sci Transl Med., 5:177ra38 (2013).
Brentjens, et al., "Eradication of systemic B-cell tumors by genetically targeted human T lymphocytes co-stimulated by CD80 and interieukin-15", Nat Med., 9:279-86 (2003).
Brown, et al., "Stem-like tumor-initiating cells isolated from IL13Rα2 expressing gliomas are targeted and killed by IL13-zetakine-redirected T Cells" Clin Cancer Res., 18(8):2199-209 (2012).
Carreno, et al., "The B7 family of ligands and its receptors: new pathways for costimulation and inhibition of immune responses", Annu Rev Immunol, 20:29-53 (2002).
Cartellieri, et al., "Chimeric Antigen Receptor-Engineered T Cells for Immunotherapy of Cancer", J Biomed Biotech., 2010, Article ID 956304, 13 pages doi:10.1155/2010/956304 (2010).
Charo, et al., "Bcl-2 overexpression enhances tumor-specific T-cell survival", Cancer Res., 65(5):2001-8 (2005).
Chen, et al., "Anti-PD-1/PD-L1 therapy of human cancer: past, present, and future", J Clin Invest.,125:3384-91 (2015).
Chen, et al., "Oncology meets immunology: the cancer-immunity cycle", Immunity, 39:1-10 (2013).
Chmielewski, et al., T cell activation by antibody-like immunoreceptors: increase in affinity of the single-chain fragment domain above threshold does not increase T cell activation against antigen-positive target cells but decreases selectivity J Immunol., 173:7647-7653 (2004).

(56) References Cited

OTHER PUBLICATIONS

Chougnet, et al., "A major role for Bim in regulatory T cell homeostasis.", J Immunol., 186:156-63 (2011).
Cooper, et al., "Enhanced antilymphoma efficacy of CD19-redirected influenza MP2-specific CTLs by cotansfer of T cells modified to present influenza MP1", Blood, 105:1622-31 (2005).
Cooper, et al., "Manufacturing of gene-modified cytotoxic T lymphocytes for autologous cellular therapy for lymphoma", Cytotherapy, 8:105-17 (2006).
Curran, et al., "Chimeric antigen receptors for T cell immunotherapy: current understanding and future directions", J Gene Med., 14:405-15 (2012).
Davies, et al., "Flexible targeting of ErbB dimers that drive tumorigenesis by using genetically engineered T cells", Mol Med., 18:565-76 (2012).
Dotti, "The other face of chimeric antigen receptors", Mol Ther., 22(5):899-900 (2014b).
Dotti, et al., "Design and development of therapies using chimeric antigen receptor-expressing T cells", Immunol Rev., 257(1):107-26 (2014).
Du, et al., "New immunotoxins targeting CD123, a stem cell antigen on acute myeloid leukemia cells", J Immunother, 30:607-13 (2007).
Dudley and Rosenberg, "Afoptive cell transfer therapy", Semin Oncol., 34:524-31 (2007).
Dudley, et al., "A phase I study of nonmyeloablative chemotherapy and adoptive transfer of autologous tumor antigen-specific T lymphocytes in patients with metastatic melanoma", J Immunother., 25:243-51 (2002).
Eaton, et al., "Retroviral transduction of human peripheral blood lymphocytes with Bcl-X(L) promotes in vitro lymphocyte survival in pro-apoptotic conditions", Gene Therapy, 9:527-35 (2002).
Ehninger, et al., "Distribution and levels of cell surface expression of CD33 and CD123 in acute myeloid leukemia", Blood Cancer J., 4:e218 (2014).
Elango, et al., "Optimized transfection of mRNA transcribed from a d(A/T) 100 tail-containing vector", Biochem Biophys Res Commun., 330:958-66 (2005).
Eshhar, et al., "Functional expression of chimeric receptor genes in human T cells", J Immunol Methods, 248:67-76 (2001).
Fedorov, et al., "PD-1- and CTLA-4-based inhibitory chimeric antigen receptors (iCARs) divert off-target immunotherapy responses", Sci Transl Med., 5:215ra172 (2013).
Ferber, "Gene therapy: Safer and virus free", Science, 294:1638-42 (2001).
Finney, et al., "Chimeric receptors providing both primary and costimulatory signaling in T cells from a single gene product", J Immunol., 161:2791-7 (1998).
Gattinoni, et al., "Acquisition of full effector function in vitro paradoxically impairs the in vivo antitumor efficacy of adoptively transferred CD8 T cells", J Clin Invest., 115:1616-26 (2005).
Gavathiotis, et al., "BAX activation is initiated at a novel interaction site", Nature, 455:1076-81 (2008).
Gilbert, et al., "CRISPR-mediated modular RNA-guided regulation of transcription in eukaryotes", Cell, 154:442-51 (2013).
Gill, et al., "Going viral: chimeric antigen receptor T-cell therapy for hematological malignancies", Immunol Rev.,263:68-89 (2015).
Grada, et al., "TanCAR: A Novel Bispecific Chimeric Antigen Receptor for Cancer Immunotherapy", Mol Ther Nucleic Acids, 2:e105 (2013).
Greenwald, et al., "The B7 family revisited", Annu Rev Immunol, 23:515-48 (2005).
Griffiths, et al., "Herpesvirus saimiri-based gene delivery vectors", Curr Gene Ther., 6:1-15 (2006).
Gross, and Eshhar, "Endowing T cells with antibody specificity using chimeric T cell receptors", FASEB, 6:3370-8 (1992).
Hacein-Bey-Abina, et al., "A serious adverse event after successful gene therapy for X-linked severe combined immunodeficiency", NEJM, 348:255-6 (2003).

Haynes, et al., "Redirecting mouse CTL against colon carcinoma: superior signaling efficacy of single-chain variable domain chimeras containing TCR-zeta vs Fc epsilon RI-gamma", J Immunol., 166:182-7 (2001).
Heemskerk, et al., "Adoptive cell therapy for patients with melanoma, using tumor-infiltrating lymphocytes genetically engineered to secrete interleukin-2", Hum Gene Ther., 19:496-510 (2008).
Herweijer and Wolff, "Progress and prospects: naked DNA gene transfer and therapy", Gene Ther. 10(6):453-8 (2003).
Hinrichs, et al., "Exploiting the curative potential of adoptive T-cell therapy for cancer", Immunol Rev., 257:56-71 (2014).
Hombach, et al., "T cell activation by recombinant FcepsilonRI gamma-chain immune receptors: an extracellular spacer domain impairs antigen-dependent T cell activation but not antigen recognition", Gene Ther., 7:1067-75 (2000).
Hudecek, et al., "Receptor affinity and extracellular domain modifications affect tumor recognition by ROR1-specific chimeric antigen receptor T cells", Clin Cancer Res., 19:3153-64 (2013).
Hunter, et al., "Chimeric γc cytokine receptors confer cytokine independent engraftment of human T lymphocytes", Mol Immunol., 56:1-11 (2013).
Irving, et al., "The cytoplasmic domain of the T cell receptor zeta chain is sufficient to couple to receptor-associated signal transduction pathways", Cell, 64:891-901 (1991).
Jensen, et al., "Design and implementation of adoptive therapy with chimeric antigen receptor-modified T cells", Immunol Rev., 257(1):127-44 (2014).
Kahlon, et al., "Specific recognition and killing of glioblastoma multiforme by interleukin 13-zetakine redirected cytolytic T cells", Cancer Res., 64:9160-6 (2004).
Kalos, et al., "T cells with chimeric antigen receptors have potent antitumor effects and can establish memory in patients with advanced leukemia", Sci Transl Med., 3:95ra73 (2011).
Kapp and Lorsch, "The molecular mechanics of eukaryotic translation", Annu Rev Biochem., 73:657-704 (2004).
Karlsson, et al., "Combining CAR T cells and the Bcl-2 family apoptosis inhibitor ABT-737 for treating B-cell malignancy", Cancer Gene Therapy, 20:386-93 (2013).
Kavanagh, et al., "Expansion of HIV-specific CD4 and CD8 T cells by dendritic cells transfected with MRNA encoding cytoplasm- or lyso-some-targeted nef", Blood, 107:1963-9 (2006).
Keir, et al., "PD-1 and its ligands in tolerance and immunity", Annu Rev Immunol, 26:677-704 (2008).
Kenderian, et al., "CD33-specific chimeric antigen receptor T cells exhibit potent preclinical activity against human acute myeloid leukemia", Leukemia, 29(8):1637-47 (2015).
Kershaw, et al., "Supernatural T cells: genetic modification of T cells for cancer therapy", Nat Rev Immunol., 5:928-40 (2005).
Kochenderfer, et al., "Donor-derived CD19-targeted T cells cause regression of malignancy persisting after allogeneic hematopoietic stem cell transplantation", Blood, 122:4129-39 (2013).
Kochenderfer, et al., "Treating B-cell cancer with T cells expressing anti-CD19 chimeric antigen receptors", Nat Rev Clin Oncol, 10:267-76 (2013b).
Kong, et al., "Suppression of human glioma xenografts with second-generation IL13R-specific chimeric antigen receptor-modified T cells", Clin Cancer Res., 18:5949-60 (2012).
Kuwana, et al., "Expression of chimeric receptor composed of immunoglobulin-derived V regions and T-cell receptor-derived C regions", Biochem Biophys Res Commun., 149:960-8 (1987).
Labelle, et al., "A stapled BIM peptide overcomes apoptotic resistance in hematologic cancers", J Clin Invest., 122(6):2018-31 (2012).
Lamers, et al., "Treatment of metastatic renal cell carcinoma with CAIX CAR-engineered T cells: clinical evaluation and management of on-target toxicity", Mol Ther., 21:904-12 (2013).
Larson, et al., "CRISPR interference (CRISPRi) for sequence-specific control of gene expression", Nat Protoc, 8:2180-96 (2013).
Leahy, "A structural view of CD4 and CD8", FASEB,9:17-25 (1995).
Li, et al., "Apoptosis induced by DNA uptake limits transfection efficiency", Exp Cell Res., 253:541-50 (1999).

(56) References Cited

OTHER PUBLICATIONS

Li, et al., "Cleavage of BID by caspase 8 mediates the mitochondrial damage in the Fas pathway of apoptosis", Cell, 94:491-501 (1998).
Luo, et al., "Bid, a Bcl2 interacting protein, mediates cytochrome c release from mitochondria in response to activation of cell surface death receptors", Cell, 94:481-90 (1998).
Maher, "Immunotherapy of malignant disease using chimeric antigen receptor engrafted T cells", ISRN Oncol. 2012:278093 (2012).
Marin, et al., "Enhancement of the anti-leukemic activity of cytokine induced killer cells with an anti-CD19 chimeric receptor delivering a 4-1BB-C activity signal", Exp Hematol., 35:1388-97 (2007).
Mihara, et al., "Chimeric receptors with 4-1BB signaling capacity provoke potent cytotoxicity against acute lymphoblastic leukemia", Leukemia, 18:676-84 (2004).
Mizui, et al., "IL-2 protects lupus-prone mice from multiple end-organ damage by limiting CD4-CD8- IL-17-producing T cells", J Immunol.,193:2168-77 (2014).
Modak, et al., "Monoclonal antibody 8H9 targets a novel cell surface antigen expressed by a wide spectrum of human solid tumors", Cancer Res., 61:4048-54 (2001).
Moeller, et al., "A functional role for CD28 costimulation in tumor recognition by single-chain receptor-modified T cells", Cancer Gene Ther., 11:371-9 (2004).
Morgan, et al., "Case report of a serious adverse event following the administration of T cells transduced with a chimeric antigen receptor recognizing ERBB2", Mol Ther., 18:843-51 (2010).
Morris, et al., "Generation of tumor-specific T-cell therapies", Blood Rev., 20:61-9 (2006).
Muranski, et al., "Increased intensity lymphodepletion and adoptive immunotherapy—how far can we go?", Oncology, 3:668-81 (2006).
National Cancer Institute. "CAR T-cell therapy: engineering patients immune cells to treat their cancers", 3 pages, http://www.cancer.gov/about-cancer/treatment/research/car-t-cells, retrieved Nov. 11, 2015.
Oltersdorf, et al., "An inhibitor of Bcl-2 family proteins induces regression of solid tumours", Nature, 435:677-81 (2005).
Pentcheva-Hoang, et al., "Negative regulators of T-cell activation: potential targets for therapeutic intervention in cancer, autoimmune disease, and persistent infections", Immunol Rev, 229:67-87 (2009).
Pestova, et al., "Molecular mechanisms of translation initiation in eukaryotes", PNAS, 98:7029-36 (2001).
Pizzitola, et al., "Chimeric antigen receptors against CD33/CD123 antigens efficiently target primary acute myeloid leukemia cells in vivo", Leukemia, 28:1596-1605 (2014).
Porter, et al., "Chimeric antigen receptor-modified T cells in chronic lymphoid leukemia", NEJM, 365(8):725-33 (2011).
Rabinovich and Weissman, "Cell engineering with synthetic messenger RNA", Methods Mol Biol., 969:3-28 (2013).
Rabinovich, et al., "Chimeric receptor mRNA transfection as a tool to generate antineoplastic lymphocytes", Human Gene Therapy, 20:51-61 (2009).
Ramos and Dotti, "Chimeric antigen receptor (CAR)-engineered lymphocytes for cancer therapy", Expert Opin Biol Ther., 11:855-73 (2011).
Ren-Heidenreich, et al., "Comparison of the TCR zeta-chain with the FcR gamma-chain in chimeric TCR constructs for T cell activation and apoptosis", Cancer Immunol. Immunother., 51:417-23 (2002).
Rosenberg, "Shedding light on immunotherapy for cancer", NEJM . 350:1461-3 (2004).
Saeboe-Lassen, et al., "mRNA-based electro transfection of human dendritic cells and induction of cytotoxic T lymphocyte responses-against the telomerase catalytic subunit (hTERT)", J Immunol Meth., 259:191-203 (2002).
Scheel-Toellner, et al., "Differential regulation of nuclear and mitochondrial Bcl-2 in T cell apoptosis", Apoptosis, 13:109-117 (2008).

Schumann, et al., "Generation of knock-in primary human T cells using Cas ribonucleoproteins", PNAS, 112:10437-42 (2015).
Schwarz, et al., "ILA, the human 4-1BB homologue, is inducible in lymphoid and other cell lineages", Blood, 85(4):1043-52 (1995).
Shaffer , et al., "T cells redirected against CD70 for the immunotherapy of CD70-positive malignancies", Blood, 117:4304-14 (2011).
So, et al., "Immune regulation and control of regulatory T cells by OX40 and 4-1BB", Cytokine Growth Factor Rev., 198(3-4):253-62 (2008).
Song, et al., "ABT-737 induces expression of the death receptor 5 and sensitizes human cancer cells to TRAIL-induced apoptosis", J Biol Chem., 283:25003-13 (2008).
Souers, et al., "ABT-199, a potent and selective BCL-2 inhibitor, achieves antitumor activity while sparing platelets", Nature Medicine, 19:202-8 (2013).
Sutherland, et al., "SGN-CD33A: a novel CD33-targeting antibody—drug conjugate using a pyrrolobenzodiazepine dimer is active in models of drug-resistant AML", Blood, 122:1455-63 (2013).
Tamada, et al., "Redirecting gene-modified T cells toward various cancer types using tagged antibodies", Clin Cancer Res.,18:6436-45 (2012).
Tarun and Sachs, "A common function for mRNA 5' and 3' ends in translation initiation in yeast", Genes Dev., 9:2997-3007 (1995).
Till, et al., "Adoptive immunotherapy for indolent non-Hodgkin lymphoma and mantle cell lymphoma using genetically modified autologous CD20-specific T cells.", Blood, 112:2261-71 (2008).
Till, et al., "CD20-specific adoptive immunotherapy for lymphoma using a chimeric antigen receptor with both CD28 and 4-1BB domains: pilot clinical trial results", Blood, 119:3940-50 (2012).
Tse, et al., "ABT-263: a potent and orally bioavailable Bcl-2 family inhibitor", Cancer Res, 68:3421-8 (2008).
Urbanska, et al., "A universal strategy for adoptive immunotherapy of cancer through use of a novel T-cell antigen receptor", Cancer Res., 72:1844-52 (2012).
Van Tendeloo, et al., "Highly efficient gene delivery by mRNA electroporation in human hematopoietic cells: superiority to lipofection and passive pulsing of mRNA and to electroporation of plasmid cDNA for tumor antigen loading of demdritic cells",, Blood, 98:49-56 (2001).
Wang, et al., "Treatment of CD33-directed chimeric antigen receptor-modified T cells in one patient with relapsed and refractory acute myeloid leukemia", Mol Ther.,23:184-91 (2015).
Wucherpfennig, et al., "Structural biology of the T-cell receptor: Insights into receptor assembly, ligand recognition, and initiation of signaling", Cold Spring Harb Perspect Biol.,2:a005140 1-14 (2010).
Young, et al., "Viral gene therapy strategies: from basic science to clinical applicatiom", J Pathol., 208:299-318 (2006).
Zetsche, et al., "Cpf1 is a single RNA-guided endonuclease of a class 2 CRISPR-Cas system", Cell, 163(3):759-71 (2015).
Zhang, et al., "Chimeric NK-receptor-bearing T cells mediate antitumor immunotherapy", Blood, 106:1544-51 (2005).
Zhang, et al., "Lymphopenia and interleukin-2 therapy alter homeostasis of CD4+CD25+ regulatory T cells", Nat Med.,11:1238-43 (2005b).
Cooper, et al., "T-cell clones can be rendered specific for CD19: toward the selective augmentation of the graft-versus-B-lineage leukemia effect", Blood, 101(4):1637-4405-17 (2003).
Zhong, et al., "Chimeric antigen receptors combining 4-1BB and CD28 signaling domains augment PI3 kinase/AKT/Bcl-XL activation and CD8 T cell-mediated tumor eradication," Molecular Therapy, 18(2), 413-420 (2010).
Loskog, et al., "Addition of the CD28 signaling domain to chimeric T-cell receptors enhances chimeric T-cell resistance to T regulatory cells," Leukemia, 20, 1819-1828 (2006).

* cited by examiner (SEQ ID NO:3)

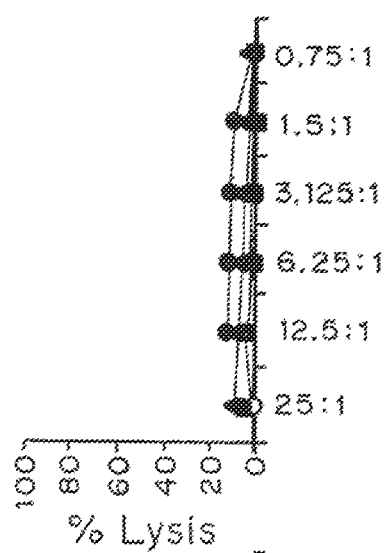
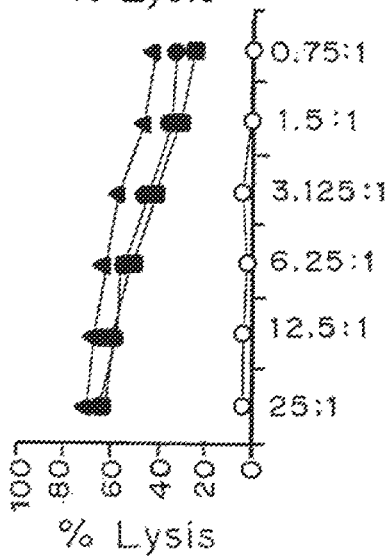
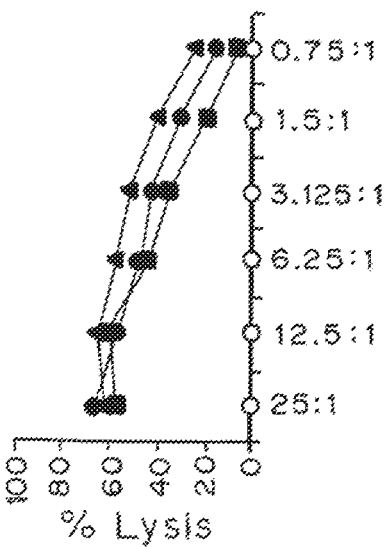
FIG. 6E
FIG. 6F
FIG. 6G

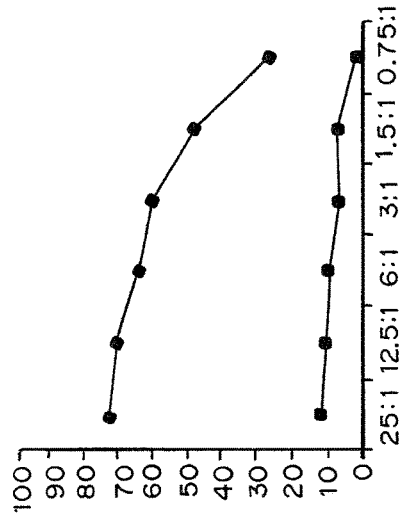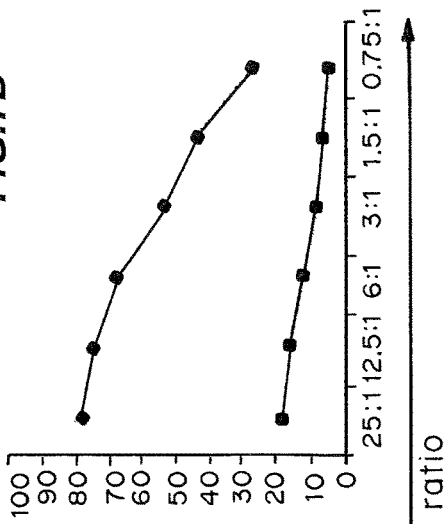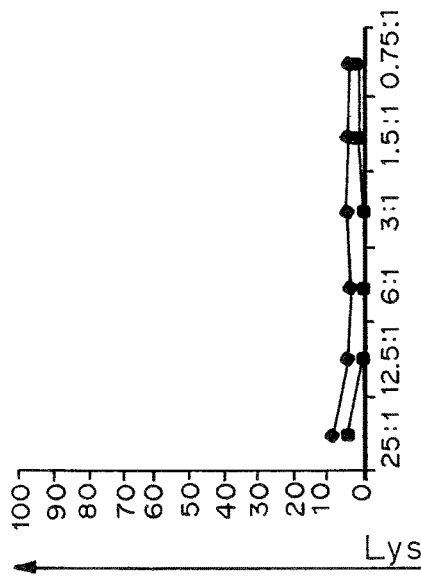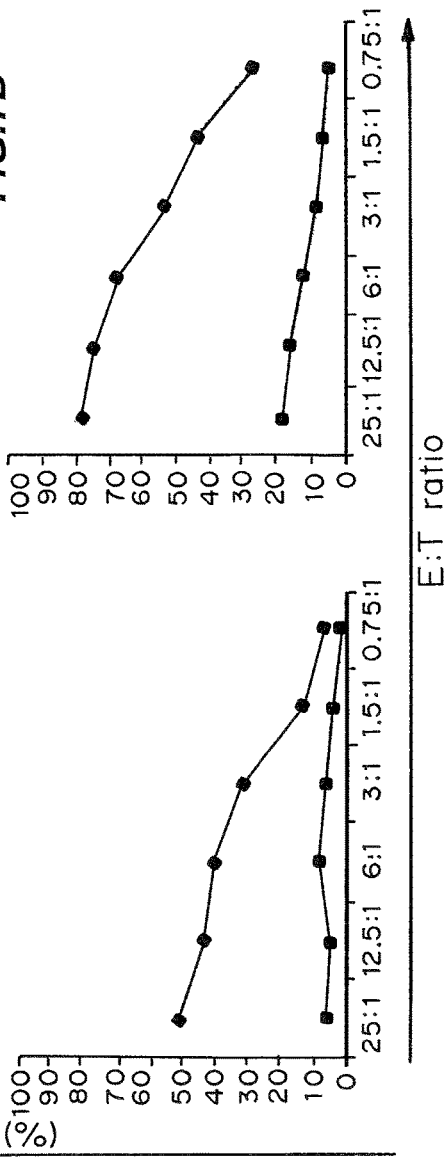

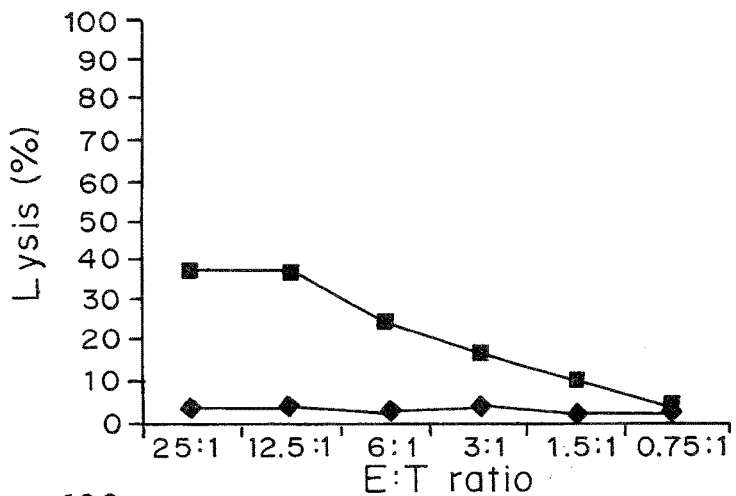
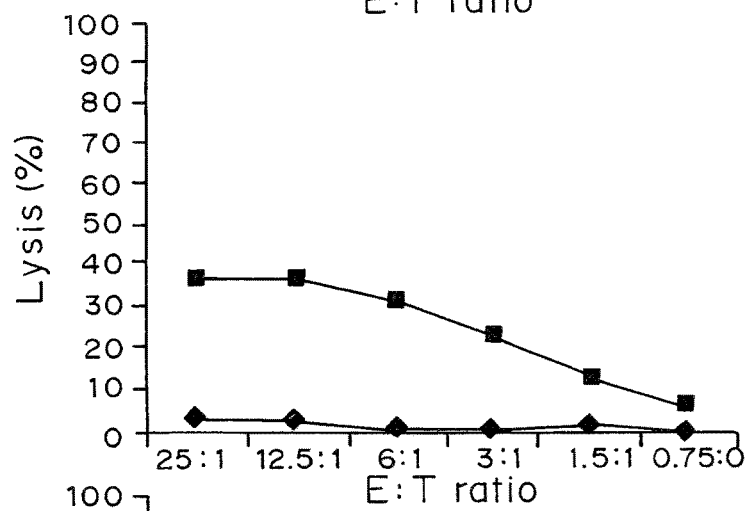
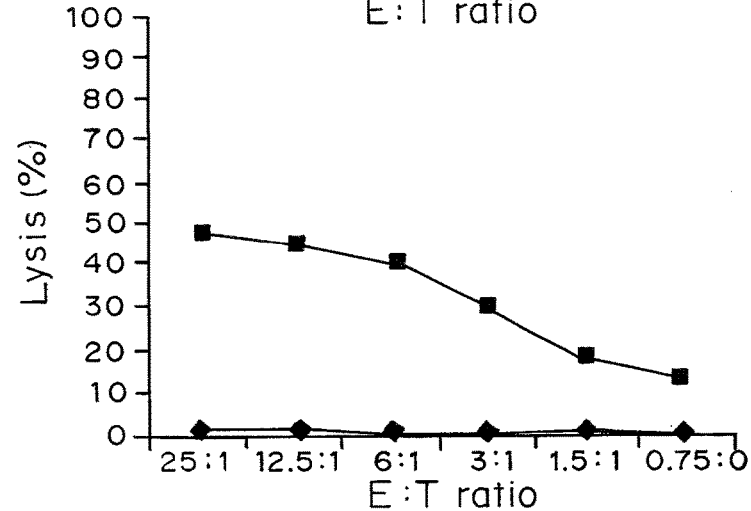
FIG. 8A
FIG. 8B
FIG. 8C

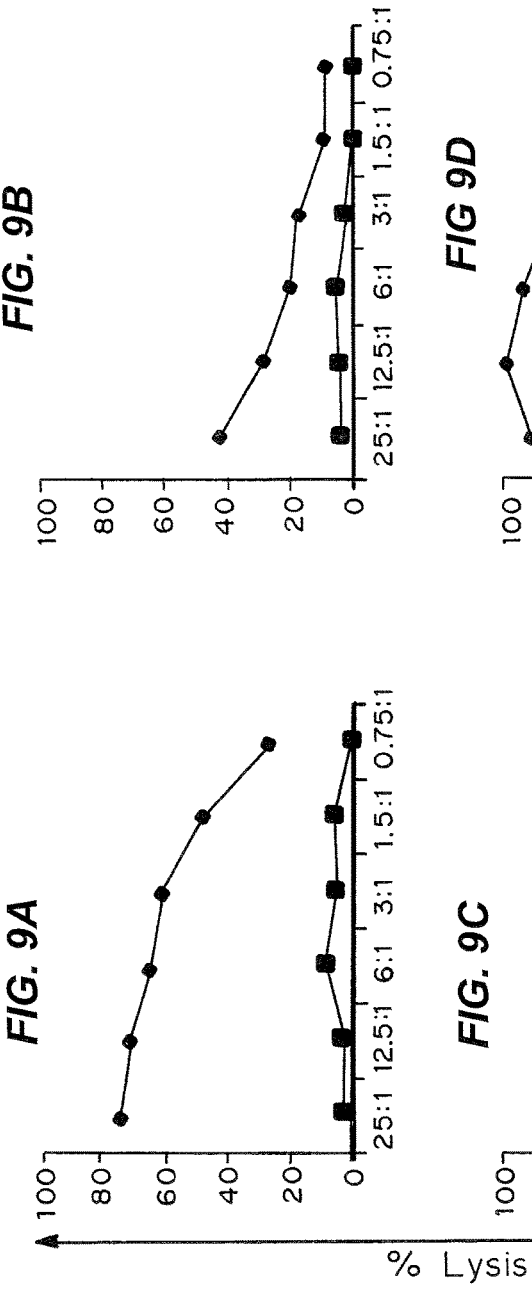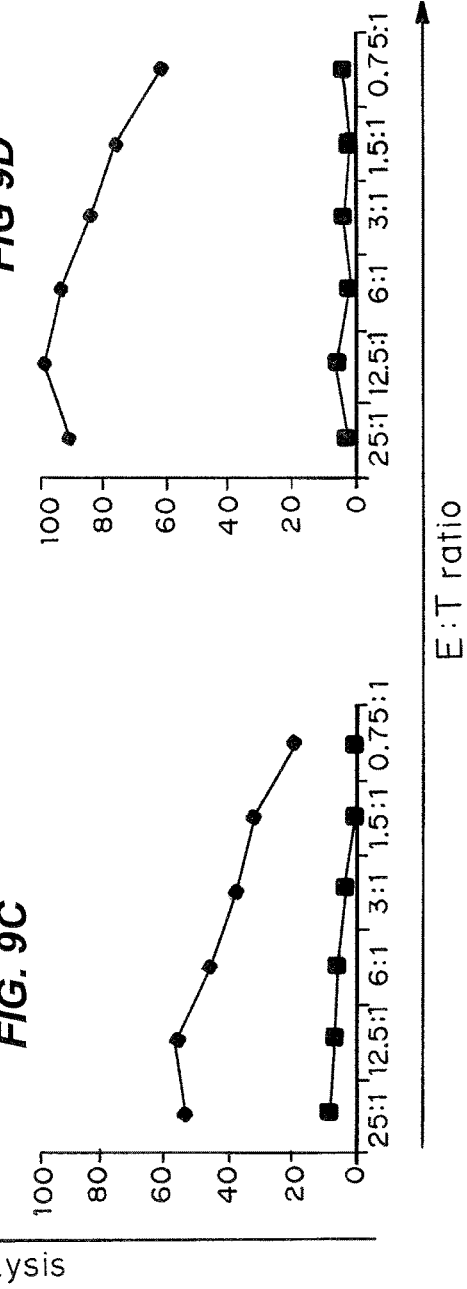

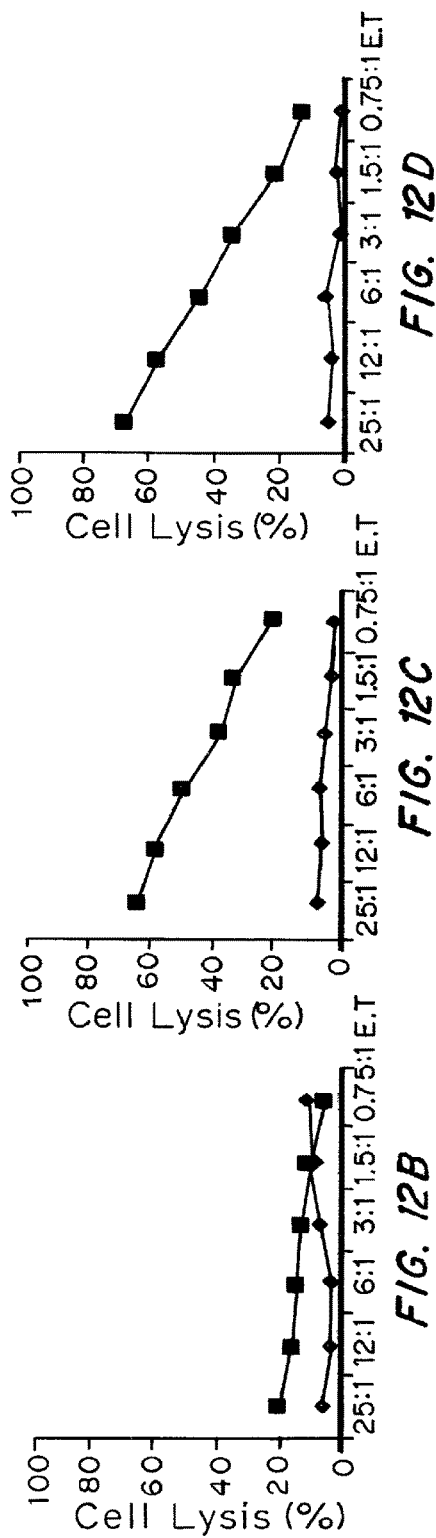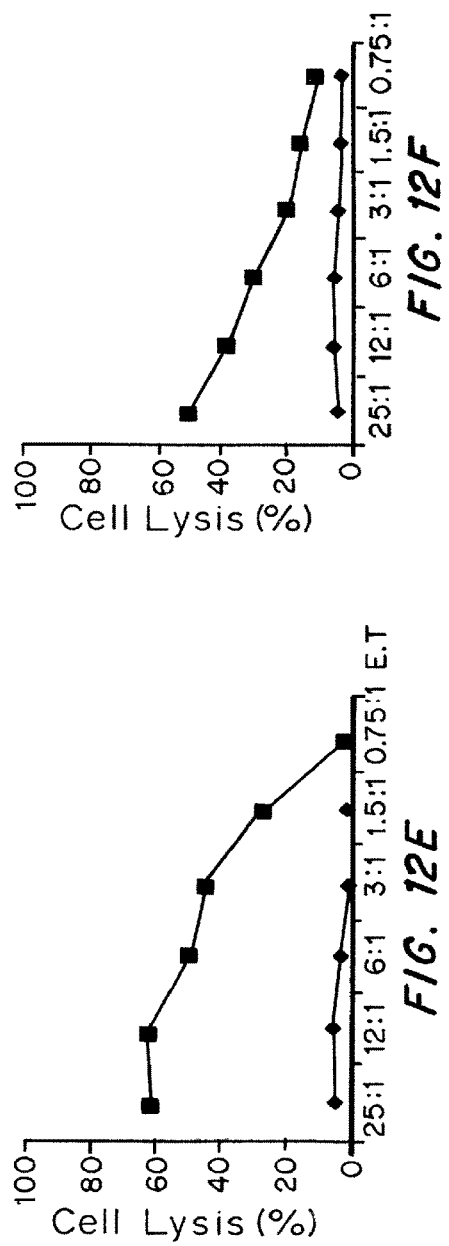

IMMUNE CELLS MODIFIED BY TRANSIENT TRANSFECTION OF RNA

CROSS-REFERENCE TO RELATED APPLICATIONS

This application is a continuation of U.S. Ser. No. 13/019,829 filed Feb. 2, 2011, now U.S. Pat. No. 9,249,423, which is a continuation-in-part of U.S. Ser. No. 12/025,700 filed Feb. 4, 2008, now U.S. Pat. No. 8,859,229, which claims benefit of and priority to U.S. Ser. No. 60/899,144 filed on Feb. 2, 2007. U.S. Ser. No. 12/025,700 and U.S. Ser. No. 60/899,144 are incorporated by reference in their entirety.

STATEMENT REGARDING FEDERALLY SPONSORED RESEARCH OR DEVELOPMENT

This invention was made with government support under AA015632, AA011197, DA013334 and HV028186 awarded by the National Institutes of Health. The government has certain rights in the invention.

FIELD OF THE INVENTION

The present invention is generally in the field of genetic engineering employing RNA-mediated gene delivery.

REFERENCE TO SEQUENCE LISTING

The Sequence Listing submitted as a text file named "YU_4277_CIP_CON_ST25.txt," created on Jul. 12, 2017, and having a size of 1,256 bytes is hereby incorporated by reference pursuant to 37 C.F.R § 1.52(e)(5).

BACKGROUND OF THE INVENTION

The advent of recombinant DNA technology has led to substantial effort to develop methods to facilitate the transfection and transduction of therapeutic and other nucleic acid-based agents to specific cells and tissues. Known techniques provide for the delivery of such agents with a variety of genes, provided in recombinant expression constructs. These constructs are capable of mediating functionality of the genes once they arrive within a cell. Such developments have been critical to many forms of molecular medicine, specifically gene therapy, whereby a missing or defective gene can be replaced by an exogenous copy of the functional gene.

Introduction of foreign nucleic acid into a cell can be accomplished by different methods. Current methods include viral transduction and non-viral delivery, such as electroporation, lipid dependent, polymer dependent, polypeptide dependent delivery, calcium co-precipitation and transfection with "naked" DNA.

Viral approaches typically use a genetically engineered virus to infect a host cell, thereby "transducing" the cell with an exogenous nucleic acid. Among known viral vectors are recombinant DNA viruses, poxviruses, herpes viruses, adenoviruses, and retroviruses. Such recombinants can carry heterologous genes under the control of promoters or enhancer elements, and are able to cause their expression in vector-infected host cells, as reviewed in Mackett et al., *J. Virol.* 49:3 (1994); Kotani et al., *Hum. Gene Ther.* 5:19-28 (1994). Transgene delivery by DNA viruses carries a risk of mutagenicity due to foreign DNA integration into the cellular genome. The use of RNA viruses as vectors is complicated by their cytotoxicity and the risk of undesirable viral propagation. Introduction of viral vectors can result in inactivation or ectopic activation of cellular genes, thereby causing diseases (Lee et al., *J. Virol.* 64:5958-5965 (1990)) or activation of oncogenes (Shiramizu et al., *Cancer Res.*, 54:2069-2072 (1994)). Furthermore, viral vectors are susceptible to undesirable interactions with the host immune system.

Non-viral methods of gene delivery were initially developed on DNA models and include electroporation, liposomal, polymer, polypeptide dependent delivery and transfection with "naked" DNA. Electroporation utilizes the application of brief, high-voltage electric pulses to a variety of animal and plant cells and leads to the formation disturbances in the plasma membrane (U.S. Pat. No. 4,394,448 to Szoka, Jr., et al. and U.S. Pat. No. 4,619,794 to Hauser). Nucleic acids can enter directly into the cell cytoplasm either through these, or as a consequence of the redistribution of membrane components that accompanies membrane restoration. Liposomal and polypeptide dependent approaches mix the material to be transferred with non-toxic polymers to form particles able to penetrate cells and to deliver nucleic acids into cytoplasm (Felgner and Ringold, *Nature*, 337:387-388 (1989), Saltzman and Desai, *Annals of Biomedical Engineering*, 34, 270-275 (2006). "Naked" DNA transfection approaches involve methods where nucleic acids are administered directly in vivo (Herweijer and Wolff, *Gene Ther.* 10(6):453-8 (2003)).

An alternative procedure for non-viral gene delivery is achieved by transfection of mRNA rather than DNA. In principle, unlike DNA transfection, introducing mRNA can have no permanent effect on the genetic structure of the cell, at least in the absence of rare reverse transcription events. There is limited literature on the application of mRNA transfection approaches (for example, Seaboe-Larssen, et al., *J. Imm. Methods*, 259:191-203 (2002); Boczkowski et al., *Cancer Res.*, 60:1028-1034 (2001); and Elango et al., *Biochem. Biophys. Res. Comm.*, 330, 958-966 (2005)), and little in the way of a systematic comparison of DNA and RNA transfection procedures. Most available literature for mRNA transfection is based on methods that involve labor intensive cloning of the gene of interest in special vectors containing a bacteriophage promoter upstream and polyA/T stretch downstream of the cloning site. Not only is cloning time consuming, but recombinant plasmids containing a stretch of poly(A/T) are often unstable in bacterial cells and prone to spontaneous mutations (Kiyama, et al., *Gene*, 150:1963-1969 (1994)). Furthermore, most mRNAs that are generated from d(A/T)n vectors contain a short sequence of heterologous nucleotides following the poly(A) tail. The influence of these heterologous sequences on translation is unknown (Elango et al., *Biochem. Biophys. Res. Comm.*, 330, 958-966 (2005)). There is therefore a need for a transfection method that circumvents the problems associated with vector-dependent transfection methods.

It is an object of the present invention to provide a more convenient and/or efficient method of mRNA production for transfection of different types of cells, including cells which are not transfectable for DNA.

It is also an object of the present invention to provide a method of mRNA transfection with minimal side effects and high efficiency, which allows transient expression of genes and desirable modification of cell phenotype without causing permanent genetic changes, which avoids risk associated with conventional gene therapy.

It is also an object of the present invention to provide a method of cell transfection with multiple genes wherein the level of each gene expression can be individually controlled.

It is an object of the present invention to provide a method of transfection of primary mammalian cells, including human cells, and use of those cells for treatment of a variety of human diseases including neurological diseases, organ regeneration, and restoration of the immune system.

It is another object of the present invention to provide a method of transient cell modification, which allows fast and safe generation of diverse differentiation, de-differentiation, re-differentiation, or reprogrammed states of cells of different cell types, including diverse stem cells from various tissues such as fibroblasts, hematopoietic, epithelial cells and others.

SUMMARY OF THE INVENTION

A method of mRNA production that involves in vitro transcription of PCR generated templates with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length, for use in transfection, is provided. This RNA can efficiently transfect different kinds of cells. This approach results in increased efficiency (fidelity and productivity) of mRNA synthesis and is less time consuming because it does not require cloning, thereby eliminating the unwanted errors and effects related to RNA made on DNA templates obtained with cloning techniques.

The results of transfection of RNAs obtained using this method demonstrate that RNA transfection can be very effective in cells that are exceedingly difficult to transfect efficiently with DNA constructs. Further, the levels of gene expression following mRNA transfection are consistent from cell to cell and these levels can be controlled over a wide range simply by changing the amount of mRNA that is transfected. Due to the high efficiency of transfection, the cells can be simultaneously transfected with multiple genetic constructs. The method can be used to deliver genes or inhibitory nucleic acids into cells not- or only poorly transfectable for DNA, in vitro and in vivo, and modulate cell activity. The methods can be used to de-differentiate, re-differentiate, or re-program cells. For example, cells can be induced to form induced pluripotent stem (iPS) cells. Cells prepared according the disclosed methods are useful in research, and cell therapy, for example by administering the cells to a subject in need thereof for the treatment of a disease or disorder.

BRIEF DESCRIPTION OF THE DRAWINGS

FIGS. 6E-6G are line graphs showing cytotoxicity of CD8+T lymphocytes (CTLs) transfected with various amounts of anti-CD19-CAR mRNA and analyzed for cytotoxicity with different targets at the indicated E:T ratio. T lymphocytes were incubated for 4 hr with different target cells, loaded with $^{51}$Cr: FIG. 6E, autologous cells CD19+ B cells; FIG. 6F, allogeneic CD19+ B lymphoblasts; FIG. 6G, CD19 negative K562 cells. (-○-)=mock; (-■-)=13.3 µg/ml; (-▲-)=40 µg/ml; (-●-)=120 µg/ml.

FIGS. 7A-7D show cytotoxicity of anti-CD19 CIR+ CTLs against CD19+ tumor cells. CTLs were mock transfected (-■-) or transfected with anti-CD19 CIR mRNA (-▲-). Target cells (K562-negative control, and other cells expressing CD19 antigen), were loaded with $^{51}$Cr and analyzed for cytotoxicity at the indicated E:T ratio. FIGS. 7A, 7B, 7C and 7D show the results for CD19 K562 cells, Daudi non-Hodgkin's lymphoma cells, autologous B cells, and NALM6 lymphoblastic leukemia cells, respectively.

FIGS. 8A-8C show CIR activity in different conditions. Cells were either mock transfected (-▲-) or transfected (-■-) with anti-CD19 CIR (FIGS. 8A and 8B) or anti-CD19 deltaCIR (FIG. 8C) mRNA. CTLs were activated for 1 day (FIG. 8A) or 7 days (FIGS. 8B and 8C) in the presence of CD3-CD28 beads and IL2. FIGS. 8A, 8B and 8C show the cytotoxicity (percent lysis) of transfected CTLs against autologous B cells at the indicated E:T ratios.

FIGS. 9A-9D show the cytotoxicity of different lymphocyte subpopulations against autologous B cells. The different lymphocytes subpopulations were: CD8+ (FIG. 9A), CD4+ T cells (FIG. 9B) and their (1:1) mix (FIG. 9C), and NK cells (FIG. 9D) transfected with anti-CD19 CIR mRNA (-□-) or mock transfected (-□-). Targets, autologous CD19+ B cells, were loaded with $^{51}$Cr and analyzed for cytotoxicity at the indicated E:T ratio.

FIG. 10A shows expression of CD19 mRNA in two CD19-target cell lines, K562 (erythroleukemia) and A2058 (melanoma), either mock transfected (-■-) or transfected with CD19 receptor mRNA (-▲-). FIG. 10B shows cytotoxicity of CTLs transfected with anti-CD19 CIR mRNA against modified targets. It is shown that expression of CD19 receptor on both targets increased their sensitivity to CIR-mediated killing.

FIG. 12B-12F show the cytotoxicity of 8H9 CIR+ CTLs against solid tumors. CTLs were transfected with 8H9 CIR mRNA. CTLs were mock transfected (-♦-) or transfected with 8H8 CIR mRNA (-■-). Target cells (K562-negative control, and other cells expressing gp58 antigen), were loaded with 51Cr and analyzed for cytotoxicity at the indicated E:T ratio. Target cells were K562 erythroleukemia cells (FIG. 12B), T470 breast ductal carcinoma cells (FIG. 12C), HTB82 rhabdosarcoma cells (FIG. 12D), primary melanoma cells (FIG. 12E) or MCF7 breast adenocarcinoma cells (FIG. 12F).

FIG. 13 is a line graph showing the longitudinal monitoring of the bioluminescent signals of fflux+ Daudi cells injected into groups of two NOD/scid mice. Points are the geometric mean photon flux (in p/s/cm2/sr), normalized against initial signal for each mouse; bars, geometric SD.

DETAILED DESCRIPTION OF THE INVENTION

I. Definitions

Figure 1:
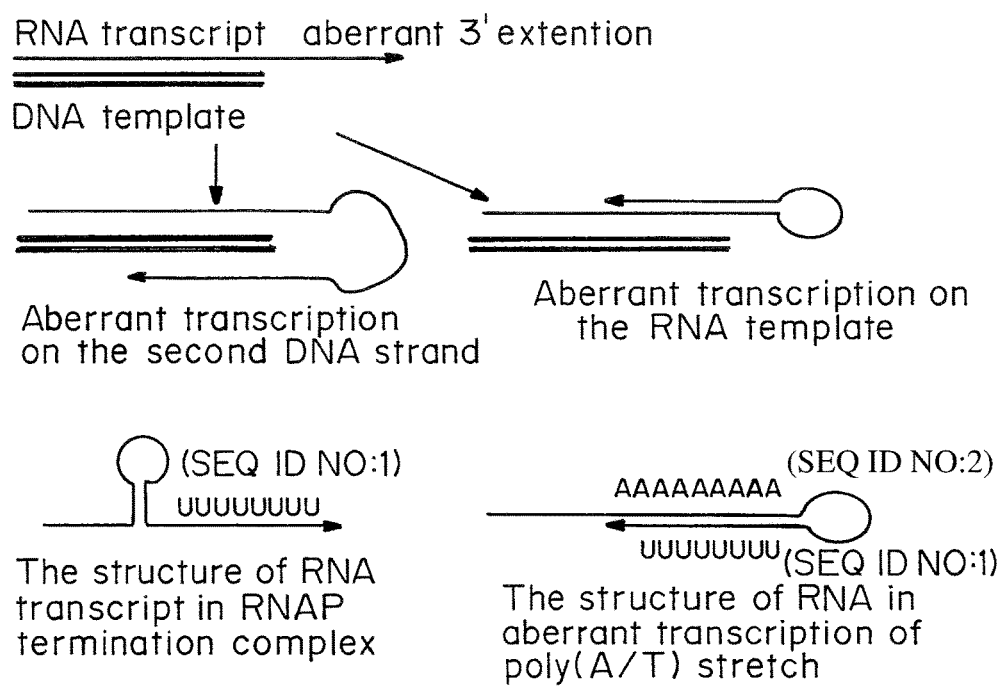
FIG. 1 shows a model of an aberrant T7 RNAP transcription in vitro, which explains why only those DNA templates which contain a polyA/T sequence are suitable for efficient transcription. On a linear DNA template, phage T7 RNA polymerase can extend the 3' end of the transcript beyond the last base of the template This could lead to runoff transcript bending followed by template exchange with the second DNA strand or transcription of RNA itself, and then to the aberrant transcription in a reverse direction and accumulation of double stranded RNA, which can inhibit gene expression. DNA linearization itself was not sufficient for correct transcription (Triana-Alonso et al., 1995; Dunn and Studier 1983; Arnaud-Barbe et al., 1998; Macdonald et al., 1993; Nakano et al., 1999). It was hypothesized that the presence of a polyT stretch at the 3'end of the DNA template during runoff transcription creates a terminator-like hairpin which can dissociate the RNA polymerase from the template.

The brief life of an mRNA molecule begins with transcription and ultimately ends in degradation. During its life, an mRNA molecule may be processed, edited, and transported prior to translation. During transcription, RNA polymerase makes a copy of a gene from the DNA to mRNA as needed. Eukaryotic RNA polymerase associates with mRNA processing enzymes during transcription so that processing can proceed quickly after the start of transcription. The short-lived, unprocessed or partially processed, product is termed pre-mRNA; once completely processed, it is termed mature mRNA. Eukaryotic pre-mRNA, however, requires extensive processing.

As used herein, a 5' cap (also termed an RNA cap, an RNA 7-methylguanosine cap or an RNA m$^7$G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

Eukaryotic mRNA that has been processed and transported to the cytoplasm (i.e. mature mRNA) can then be translated by the ribosome. Translation may occur at ribosomes free-floating in the cytoplasm, or directed to the endoplasmic reticulum. After a certain amount of time, the message is degraded by RNases into its component nucleotides. The limited longevity of mRNA enables a cell to alter protein synthesis rapidly in response to its changing needs.

Different mRNAs within the same cell have distinct lifetimes. In bacterial cells, individual mRNAs can survive from seconds to more than an hour; in mammalian cells, mRNA lifetimes range from several minutes to days. The greater the stability of an mRNA, the more protein may be produced from that transcript. The presence of AU-rich motifs in some mammalian mRNAs tends to destabilize those transcripts through the action of cellular proteins that bind these motifs. Rapid mRNA degradation via AU-rich motifs is a critical mechanism for preventing the overproduction of potent cytokines such as tumor necrosis factor (TNF) and granulocyte-macrophage colony stimulating factor (GM-CSF). Base pairing with a small interfering RNA (siRNA) or microRNA (miRNA) can also accelerate mRNA degradation.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, a "promoter site" is a sequence of nucleotides to which an RNA polymerase, such as the DNA-dependent RNA polymerase originally isolated from bacteriophage, described by Davanloo, et al., Proc. Natl. Acad. Sci. USA, 81:2035-39 (1984), or from another source, binds with high specificity, as described by Chamberlin, et al., Nature, 228:227-231 (1970).

As used herein, a poly(A) is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

II. Methods of Making mRNA for Use in Transient Transfection

RNA for transient transfection is produced by in vitro transcription using a polymerase chain reaction (PCR)-generated template.

A. Sources of DNA for PCR

DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism. Genes that can be used as sources of DNA for PCR include genes that encode peptides that are important for regulating cellular differentiation. Preferred genes include transcription factors and mRNA-binding proteins, for example, transcription factors that regulate the self-renewal and/or proliferation of stem cells. In some embodiments, the DNA encodes inhibitory RNAs, such as small interfering RNA (siRNA) or micro RNA (miRNA). For example, the DNA may encode an interfering RNA that prevents expression of an mRNA encoding an allogenic antigen. The DNA may encode an RNA that is a pre-RNA, for example pre-miRNA, or a mature RNA, for example mature miRNA. The DNA may encode an RNA that is a fragment or variant of an RNA that retains the biological activity of the RNA.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. It is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

B. PCR to Produce Templates for In Vitro Transcription

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

1. Untranslated Regions

Chemical structures with the ability to promote stability and/or translation efficiency may also be used. The RNA preferably has 5' and 3' UTRs. Inclusion of 44 base pairs of 5' UTR into the PCR template enables greater translation efficiency of transcribed RNA, for example green fluorescent protein (GFP), when compared to PCR templates containing only 6 base pairs of 5' UTR. The addition of 113 base pairs of 3' UTR enables greater translation efficiency of transcribed GFP RNA when compared to PCR templates containing only 11 base pairs of 3' UTR. In general, the length of the 3' UTR exceeds 100 nucleotides, and therefore 3' UTR longer then 100 nucleotides is preferred. For example, the 3' UTR sequence is between 100 and 5000 nucleotides. The length of the 5' UTR is not as critical as the length of the 3' UTR and can be shorter. For example, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences increase the efficiency of translation of some RNA transcripts, but do not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

2. RNA Polymerase Promoter

To enable synthesis of RNA from a DNA template without the need for gene cloning, a promoter of transcription should be attached to the DNA template upstream of the sequence to be transcribed. Bacteriophage RNA polymerase promoter sequences can be attached to the 5' UTR by different genetic engineering methods, such as DNA ligation, or can be added to the forward primer (5') of the sequence that is substantially complementary to the target DNA. When a sequence that functions as a promoter for an RNA polymerase is added to 5' end of the forward primer, the RNA polymerase promoter becomes incorporated into the PCR product upstream of the open reading frame that is to be transcribed. In one preferred embodiment, the promoter is a T7 polymerase promoter. Other useful promoters include, but are not limited to, T3 and SP6 RNA polymerase promoters. Consensus nucleotide sequences for T7, T3 and SP6 promoters are known in the art.

3. Poly(A) Tail and 5' Cap

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, *Nuc Acids Res.*, 13:6223-36 (1985); Nacheva and Berzal-Herranz, *Eur. J. Biochem.*, 270:1485-65 (2003). This could lead to runoff transcript bending followed by template exchange with the second DNA strand or transcription of RNA itself (Triana-Alonso et al., *J. Biol. Chem.*, 270:6298-307 (1995); *Dunn and Studier, J. Mol. Biol.*, 166:477-535 (1983); Arnaud-Barbe et al., *Nuc. Acids Res.*, 26:3550-54 (1998); Macdonald et al., 1993), and then to the aberrant transcription in a reverse direction and accumulation of double stranded RNA, which can inhibit gene expression. DNA linearization itself is not sufficient for correct transcription (Triana-Alonso et al., *J. Biol. Chem.*, 270:6298-307 (1995); *Dunn and Studier, J. Mol. Biol.*, 166:477-535 (1983); Arnaud-Barbe et al., 1998 *Nuc. Acids Res.*, 26:3550-54 (1998); Macdonald et al., *J. Mol. Biol.*, 232:1030-47 (1993); Nakano et al., *Biotechnol. Bioeng.*, 64:194-99 (1999). plasmid DNA linearized downstream of a poly(A/T) stretch of 64-100 nucleotides results in good templates (Saeboe-Larssen et al., *J. Immunol. Meth.*, 259:191-203 (2002); Boczkowski et al., *Cancer Res.*, 60:1028-34 (2000); Elango et al., *Biochem Biophys Res Commun.*, 330:958-966 2005). An endogenous termination signal for T7 RNA polymerase encodes an RNA that can fold into a stem-loop structure followed by a track of uridine residues (Dunn and Studier, *J. Mol. Biol.*, 166:477-535 (1983); Arnaud-Barbe et al., 1998 *Nuc. Acids Res.*, 26:3550-54 (1998)). Even without a hairpin, a track of synthesized uridines can attenuate transcription (Kiyama and Oishi, *Nucleic Acids Res.*, 24:4577-4583 (1996). It was hypothesized that the linearization of plasmid DNA downstream of the poly(A/T) stretch probably formed a type of "dynamic" terminator preventing potential aberrant transcription: a 3' extension of the RNA transcript over a poly(A/T) stretch and transcription in the reverse direction will create a growing termination-like signal—an extended poly(U) stretch and a poly(A/U) hairpin (FIG. 1). Based on this presumption, reversed PCR primers are designed with a 3' anchoring sequence downstream of the GFP gene and a 5' 100 base stretch of poly(T).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, typically 50-5000T, for example a 100T tail, or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines. The examples below demonstrate that a 100 base pair stretch of poly(A) is sufficient to enable efficient translation of an RNA transcript.

Poly(A) tails of RNAs can be further extended following in vitro transcription with the use of a poly(A) polymerase, such as E. coli polyA polymerase (E-PAP). Increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine.

5'caps can also provide stability to RNA molecules. In a preferred embodiment, RNAs include a 5' cap. The 5' cap may, for example, be m$^7$G(5')ppp(5')G, m$^7$G(5')ppp(5')A, G(5')ppp(5')G or G(5')ppp(5')A cap analogs, which are all commercially available. The 5' cap can also be an anti-reverse-cap-analog (ARCA) or any other suitable analog. The 5' cap is provided using techniques known in the art (Cougot, et al., *Trends in Biochem. Sci.*, 29:436-444 (2001); Stepinski, et al., *RNA*, 7:1468-95 (2001); Elango, et al., *Biochim. Biophys. Res. Commun.*, 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

III. Methods of Use

RNA, for example RNA prepared by in vitro transcription using a polymerase chain reaction (PCR)-generated template as described above, can be introduced into a cell to modulate cell activity. This method is particularly useful in de-differentiating somatic cells to unipotent, pluripotent or multipotent cells; re-differentiating stem cells into differentiated cells, or reprogramming of somatic cells to modulate cell activities such as metabolism. Cells can also be transfected with inhibitory RNAs, such as small interfering RNA (siRNA) or micro RNA (miRNA), or combinations thereof to induce reprogramming of somatic cells, for example, by preventing expression of allogenic antigens. A method for generating an autologous population of immune cells can include contacting the cells with one or more RNAs, wherein the one or more RNAs encode polypeptides that render the immune cells specific for tumor, virus, bacteria or fungal antigens expressed on the surface of the cells of a host.

A. Introduction of RNA into Target Cells

RNA can be introduced into target cells using different methods, for instance, commercially available methods which include, but are not limited to, electroporation (Maxcyte System (Maxcyte,Inc.), Amaxa Nucleofector-II (Amaxa Biosystems, Cologne, Germany), ECM 830 (Harvard Instruments, Boston, Mass.) or the Gene Pulser II (BioRad, Denver, Colo.), Multiporator (Eppendorf, Hamburg Germany), cationic liposome mediated transfection (TransIT, MirusBio LLC, Lipofectin, Invitrigen), polymer encapsulation, peptide mediated transfection, or biolistic particle delivery systems such as "gene guns" (see, for example, Nishikawa, et al. *Hum Gene Ther.*, 12(8):861-70 (2001).

B. Applications

The methods and reagents have a wide range of applications in therapy and research. The methods are useful for expressing one or multiple RNAs in different cell populations such as fully differentiated cells, partially differentiated cells, such as multipotent cells and non-differentiated cells, such as pluripotent cells. The RNA construct can be delivered into different types of eukaryotic cells as well as into tissues and whole organisms using transfected cells as carriers or cell-free local or systemic delivery of encapsulated, bound or naked mRNA. The methods can be used for any purpose where a transient expression is required or sufficient. The methods can be applied to modulation of cell activity in basic research and therapy, in the fields of cancer, stem cells, acute and chronic infections, genetic disorders, neurological disorders, and autoimmune diseases, including modulation of the developmental pathways.

1. Cells

Cells suitable for use with the method include, but are not limited to, primary cells and established cell lines, embryonic cells, immune cells, stem cells, and differentiated cells including, but not limited to, cells derived from ectoderm, endoderm, and mesoderm, including fibroblasts, parenchymal cells, hematopoietic cells, and epithelial cells. As used herein, stem cells include unipotent cells, multipotent cells, and pluripotent cells; embryonic stem cells, and adult stem cells such as hematopoietic stem cells, mesenchymal stem cells, epithelial stem cells, and muscle satellite cells. In one embodiment, somatic cells are de-differentiated or reprogrammed. Any suitable somatic cell can be used. Representative somatic cells include fibroblasts, keratinocytes, adipocytes, muscle cells, organ and tissue cells, and various blood cells including, but not limited to, hematopoietic cells including hematopoietic stem cells, and cells that provide short- or long-term hematopoietic engraftment. The most preferred cell types include, but are not limited to, human fibroblasts, keratinocytes and hematopoietic stem cells. The methods are particularly useful for de-differentiating and optionally re-differentiating cells, without permanent alteration of cell genomes.

2. RNAs

RNAs useful in the disclosed method include mRNAs, regulatory RNAs, or small RNAs such as siRNA or miRNA wherein the one or more mRNAs encode polypeptides that function to de-differentiate or reprogram the cell. The efficiency of transfection is high. Typically more than 90% of the transfected cell population will express the introduced RNA. Therefore, it is possible to transfect cells with one or more distinct RNAs. For example, the population of cells can be transfected with one or more distinct mRNAs, one or more distinct siRNAs, one or more distinct miRNAs, or combinations thereof. The population of cells can be transfected with multiple RNAs simultaneously in a single administration, or multiple administrations can be staggered minutes, hours, days, or weeks apart. Transfection of multiple distinct RNAs may be staggered. For example, if it is desirable for a first RNA to be expressed prior to expression of one or more additional RNAs.

It is possible to generate an autologous lymphocyte population with multiple sets of receptors to recognize and destroy targets which otherwise escape cytotoxic T lymphocyte (CTL) surveillance or to increase the specificity of the CTL towards selected targets. Similar procedures could be used with NK or NKT cells or other types of immune effector cells to target them to specific cells or tissues or increase their avidity for specific cells or tissues. The method can also be used to introduce various mRNAs and/or siRNAs that render the T cell resistant to inhibitory molecules in vivo. Also, mRNAs that encode transcription factors and/or effector proteins characteristic of $CD8^+$ cytotoxic T cells can be introduced into a mixed population of T lymphocytes in order to convert them all to a cytotoxic T cell phenotype.

The level of expression of the transfected RNA can be manipulated over a wide range by changing the amount of input RNA, making it possible to individually regulate the expression level of each transfected RNA. The effective amount of input RNA is determined based on the desired result. Furthermore, the PCR-based technique of mRNA production facilitates the design of mRNAs with different structures and domain combinations.

For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

RNAs useful in the disclosed methods are known in the art, and will be selected based on the target host cell type as well as the pathway or cellular activity to be manipulated, or the therapeutic application.

Genetic transduction of different types of cytotoxic lymphocytes to express desired receptors for adoptive immunotherapy is a valuable method to redirect the specificity of lymphocytes for tumor antigens, which are not readily recognized by the endogenous aB T-cell or NK receptors. However, a potential disadvantage of such method is genome integration of transgenes as well as the technical complexity of the method. It takes weeks or months to clone and accumulate a desirable homogeneous specific lymphocyte population suitable for the treatment. Another problem of cloning is that lymphocyte diversity, an important factor which determines immune response, is an unavoidable complication of such procedure. Cytotoxic lymphocytes are presented as heterogeneous subpopulations such as CD8+, CD4+, CD3+CD56+(CIK) T cells and CD3− CD56+ NK cells, with additional sub diversity among each of subpopulation. The whole cytotoxic potential can be influenced by cooperation of different cell types. The RNA transfection is essentially transient and a vector-free: mRNA transgene can be delivered and expressed into the lymphocytes after brief in vitro cell activation, as a minimal expressing cassette without any additional viral sequences. In these conditions genome integration of the transgene is quite improbable. Cell cloning becomes unnecessary because of the efficiency of mRNA transfection and its ability to uniformly modify the entire lymphocyte population. Moreover, different types of lymphocytes such as CD3+CD8+, CD3+CD4+ T cells and Cd56+ CIK and NK cells can be simultaneously transfected with CIR mRNA and used together to increase their potential synergistic effect. Thus, cells containing an RNA construct introduced according to the disclosed method can be used therapeutically. For example, a lymphocyte cell population could be withdrawn from a patient, transfected with different RNA constructs, and then reintroduced into the patient. The transfected cell population would then target lymphoma or other cancer cells, which contain the CD19 or other target antigen. A benefit of the use of mRNA transfected cells is that mRNA transgene has a limited half-life. The encoded protein will only be produced by the transfected cell for a limited period of time. This may reduce unintended consequences when genetically modified cells are reintroduced into a patient.

In the preferred embodiment, the technology is used for personalized therapy. For example, for treatment of tumors, the patient's blood or cells would be collected by an appropriate method such as apheresis, biopsy or venapuncture. The cells would be cultured for at least 24 hours during which time the cells are transfected with an appropriate construct to treat the tumor. The cells can be stored frozen before transfection, if necessary. These are then returned and administered back to the patient.

Constructs useful for de-differentiating cells, for example, converting adult, differentiated somatic cells into stem cells, can be constructed based on known genes, mRNAs, or other nucleotide or protein sequences. See, for example, Yu, et al., *Science*, 318:1917-1920 (2007) and Yamanaka, *Cell Prolif,* 41:51-56 (2008), which describes induced pluripotent stem (iPS) cells obtained from differentiated primary cells by ectopic expression of combinations of transcription factors such as OCT4, SOX2, NANOG, and LIN28, or OCT3/4, SOX2, KLF4 and c-MYC.

Exemplary genomic, mRNA (cDNA), and protein sequences for OCT4 are known in the art, see, for example, (OCT4) POU5F1 POU class 5 homeobox 1 [*Homo sapiens*] Gene ID: 5460, which provides mRNA (cDNA) sequences Genbank accession no. NM_001173531.1 entitled *Homo sapiens* POU class 5 homeobox 1 (POU5F1), transcript variant 3, mRNA; Genbank accession no. NM_002701.4 entitled *Homo sapiens* POU class 5 homeobox 1 (POU5F1) transcript variant 1, mRNA; and Genbank accession no. NM_203289.4 entitled *Homo sapiens* POU class 5 homeobox 1 (POU5F1), transcript variant 2, mRNA. Exemplary genomic, mRNA (cDNA), and protein sequences for SOX2 are also known in the art, see, for example, SOX2 SRY (sex determining region Y)-box 2. [*Homo sapiens*], GeneID: 6657, which provides mRNA (cDNA) sequence Genbank Accession no. NM_003106.2 entitled mRNA sequence mRNA sequence *Homo sapiens* SRY (sex determining region Y)-box 2 (SOX2), mRNA. Exemplary genomic, mRNA (cDNA), and protein sequences for NANOG are also known in the art, see for example NANOG Nanog homeobox [*Homo sapiens*], Gene ID: 79923, which provides the mRNA (cDNA) sequence Genbank accession no. NM_024865.2 entitled *Homo sapiens* Nanog homeobox (NANOG), mRNA. Exemplary genomic, mRNA (cDNA), and protein sequences for LIN28 are also known in the art, see for example LIN28A lin-28 homolog A (*C. elegans*) [*Homo sapiens*], Gene II): 79727, which provides the mRNA (cDNA) sequence Genbank accession no. NM_024674.4 entitled *Homo sapiens* lin-28 homolog A (*C. elegans*) (LIN28A), mRNA. Exemplary genomic, mRNA (cDNA), and protein sequences for KLF4 are known in the art, see, for example, KLF4 Kruppel-like factor 4 (gut) [*Homo sapiens*], Gene ID: 9314, which provides the mRNA (cDNA) sequence Genbank accession no. NM_004235.4 entitled *Homo sapiens* Kruppel-like factor 4 (gut) (KLF4), mRNA. mRNA sequences for MYC are also known in the art, see for example MYC v-myc myelocytomatosis viral oncogene homolog (avian) [*Homo sapiens*], Gene ID: 4609, which provides the mRNA (cDNA) sequence Genbank accession no. NM_002467.4 entitled *Homo sapiens* v-myc myelocytomatosis viral oncogene homolog (avian) (MYC), mRNA.

Following transfection with one or more RNAs, the cells can be maintained or expanded in culture. Methods for culturing both transfected and non-transfected cells are known in the art, and may include providing additional reagents or supplements to enhance viability and/or growth, for example, growth factors or a feeder layer of cells.

Although transfection using the disclosed mRNAs is transient, once the cells have been induced to de-differentiate, the de-differentiated cells can be maintained in their induced state using tissue culture conditions that are known in the art. For examples, differentiated somatic cells such as fibroblasts that are induced to de-differentiate into iPS cells can be maintained as iPS cells using methods consistent with culturing undifferentiated iPS cells.

The method can also be widely used for re-differentiating or reprogramming of cells, for example, to produce iPS cells that can be further modulated to form hematopoietic stem cells, mesenchymal stem cells, epithelial stem cells, and muscle satellite cells, or differentiated cells of human tissues, including, but not limited to, red blood cells, white blood cells including lymphocytes, platelets, stromal cells, fat cells, bone cells including osteoclasts, epithelial tissue including skin cells, muscle tissue including smooth muscle, skeletal muscle, and cardiac muscle, vascular tissue including endothelial cells, liver tissue including hepatocytes, and nervous tissue including neurons. Methods of inducing differentiation of iPS cells into various differentiated cells types, including, but not limited to, cardiomyocytes, hematopoietic stem cells, bone cells such as, osteoclasts, hepatocytes, retinal cells, and neurons, are known in the art (Song at al., *Cell Res.,* 19(11):1233-42 (2009), Lamba at al, *PLoS One,* 5(1):e8763 (2010), Gai et al., *Cell Biol Int.* 200933(11):1184-93 (2009). Grigoriadis et al., *Blood,* 115 (14):2769-76 (2010)). Stem cells including, but not limited to, isolated embryonic stem cells, hematopoietic stem cells, and induced pluripotent stem cells can be induced to differentiate by transient transfection with RNAs that induce differentiation. Additionally, or alternatively, cells can be re-differentiated by culturing the cells under cell type-specific conditions. For example, iPS cells can be maintained on CF-1 feeders and subsequently adapted to feeder-free conditions. iPS cells can be induced to form differentiated retinal cells by culturing the cells in the presence of noggin, Dkk-1, and IGF-1 (see for example Lamba at al, *PLoS One,* 5(1):e8763 (2010)).

In some embodiments, cells are re-programmed by transient transfection. For example, mRNA from transcription factors such as FoxP3 can be introduced into lymphocytes to increase the formation of regulatory T cells. FoxP3 (forkhead box P3) is a master regulator of development and function of regulatory T cells. Exemplary genomic, mRNA (cDNA), and protein sequences for FoxP3 are known in the art, see, for example Gene ID: 50943, which provides the mRNA (cDNA) sequences Genbank accession no. NM_014009.3 entitled *Homo sapiens* forkhead box P3 (FOXP3), transcript variant 1, mRNA; and Genbank accession no. Nm_001114377.1 entitled *Homo sapiens* forkhead box P3 (FOXP3), transcript variant 2, mRNA.

3. Therapeutic Applications

The disclosed methods are particularly useful in the field of stem cell therapy. In some embodiments, the methods are applied in the context of personalized therapy, for example, to generate iPS cells for introduction into a subject in need thereof. In vitro de-differentiation, re-differentiation, and/or reprogramming can be applied to a variety of different starting cell types and allows fast and safe generation of cells over a diverse range of de-differentiated or re-differentiated states. As used herein, in vitro de-differentiation, re-differentiation, and reprogramming includes de-differentiation, re-differentiation, and reprogramming of isolated cells ex vivo. For example, target cells are first isolated from a donor using methods known in the art, contacted with one or more RNA's causing the cells to be de-differentiated, re-differentiated, or reprogrammed in vitro (ex vivo), and administered to a patient in need thereof. Sources or cells include, but are not limited to peripheral lymphocytes, fibroblasts, keratinocytes primary cell lines, or cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

In some embodiments the cells are contacted with one or more RNA that reprogram the cells to prevent expression of one or more antigens. For example, the RNA may be an interfering RNA that prevents expression of an mRNA encoding antigens as CTLA-4 or PD-1. This method can be used to prepare universal donor cells. RNAs used to alter the expression of allogenic antigens may be used alone or in combination with RNAs that result in de-differentiation of the target cell.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200 or 1000 orders of magnitude. Once target cells have been isolated, they may be propagated by growing in suitable medium according to established methods known in the art. Established cell lines may also be useful in for the disclosed methods. The cells can be stored frozen before transfection, if necessary.

Next the cells are contacted with one or more RNAs in vitro, for example using a transfection technique known in the art. De-differentiation, re-differentiation, and/or re-programming can be monitored, and the desired cell type, for example iPS cells, can be selected for therapeutic administration.

iPS cells can be monitored and selected by identification of specific antigens, such as Nanog, Sox2, SSEA-3, SSEA-4, TRA-1-60, TRA-1-81, Oct 3/4 and alkaline phosphatase, and purified by different methods including magnetic column separation and flow cytometry.

Following de-differentiation, and/or re-differentiation and/or reprograming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of RNA-reprogrammed or dedifferentiated cells stored long-term, for later use. In one embodiment, fibroblasts, keratinocytes or hematopoietic stem cells are isolated from a patient and de-differentiation, and/or re-differentiated and/or reprogrammed in vitro to provide iPS cells for the patient.

The method can also be used to reprogram somatic cells wherein RNAs are introduced into cells in order to modulate their viability. For example, mRNA coding dominant-negative mutant p53 protein can temporarily block p53 function. This mRNA can be introduced into cells to protect them from p53-mediated apoptosis caused by metabolic disturbances during de-differentiation.

In some embodiments, cells are reprogrammed to modulate the immune response. For example, lymphocytes can be reprogrammed into regulatory T cells which can be administered to a patient in need thereof to increase or transfer immune tolerance, especially self-tolerance. The induction or administration of Foxp3 positive T cells may be useful in reducing autoimmune responses such graft rejection, and/or reducing, inhibiting or mitigating one or more symptoms of an autoimmune diseases or disorder such as diabetes, multiple sclerosis, asthma, inflammatory bowel disease, thyroiditis, renal disease, rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

4. Diseases to be Treated

The methods can be used to generate cells which may be useful in the treatment of a variety of diseases and disorders, including, but not limited to, neurodegenerative diseases such as Parkinson's, Alzheimer disease, and multiple sclerosis. The methods are also useful for organ regeneration, and for restoration or supplementation of the immune system. For example, cells at different stages of differentiation such as iPS cells, hematopoietic stem cells, multipotent cells or unipotent cells such as precursor cells, for example, epithelial precursor cells, and others can be administered intravenously or by local surgery. The methods can be used in combination with other conventional methods, such as a prescription medication regime, surgery, hormone therapy, chemotherapy and/or radiotherapy.

C. Kits

In one embodiment, a kit includes RNAs, cells, and a means for transfecting the RNA into the cells. The RNAs can be lyophilized or in solution. Kits may optionally include other materials such as cell culture reagents. In an alternative embodiment, a kit provides re-differentiated, dedifferentiated, or reprogrammed cells prepared according to the disclosed methods, and stored and/or shipped refrigerated or frozen for later use. Cells are typically stored in a solution maintaining viability. Kits containing cells should be stored or shipped using a method consistent with viability such as in a cooler containing dry ice so that cells are maintained below 4° C., and preferably below −20° C.

The kits optionally include one or more of the following: bioactive agents, media, excipients and one or more of: a syringe, a needle, thread, gauze, a bandage, a disinfectant, an antibiotic, a local anesthetic, an analgesic agent, surgical thread, scissors, a scalpel, a sterile fluid, and a sterile vessel. Components of the kit may be packaged individually and can be sterile. The kits are generally provided in a container, e.g., a plastic, cardboard, or metal container suitable for commercial sale. Any of the kits can include instructions for use.

The present invention will be further understood by the following non-limiting examples.

EXAMPLES

Material and Methods for Examples 1-10:
Cells
*Escherichia coli* cells were grown on LB broth with 100 µg/ml ampicillin Mouse: EML cells were grown on Iscove's Medium (Gibco) supplemented with 20% Donor Horse serum with BHK conditioned media and non-essential amino acids.

Human Cell Lines

Hela and Human Non-Hodgkin's B cell Lymphoma line CRL2261 cells were grown on DMEM (GIBCO) supplemented with 10% fetal bovine serum (FBS), glutamate. Bjab, BL2, Palo, NB4, Jurkat cells were grown in RPMI Medium supplemented with 10% FBS.

Primary Human Cells

Activated B cells were received by cultivating mononuclear cells (MNC) in the presence of CD40 ligand activation as described by Schultze, et al., *Proc. Natl. Acad. Sci.*, 92:8200-8204 (1995). MNCs were washed and plated on pre-formed layer of previously irradiated (96Gy) 3T3-CD40L on IMDM (Gibco), with 10% human serum (Gemini Bio-Products, CA, USA), 200U/ml IL-4 and in the presence of Cyclosporin A (Sigma). The cultured B-cells were transferred in new pre-layered plates and re-stimulated every 3-4 days. Cultures were kept up to 21 days. The percentage of CD19-positive cells was 85-95% after day 10 of cultivation.

Populations of activated CD3+ cells were obtained from MNCs using XCYTE DYNABEADS® (Xcyte Therapies) with covalently attached anti-CD3 and anti-CD28 monoclonal antibodies. MNCs were resuspended at $10\times10^6$/ml in DPBS, 0.5% HA and XCYTE DYNABEADS® (50 µl per ml of sample) were added. The mixture then was incubated 30 min in a refrigerator with rotation. The positive (CD3+) fraction was isolated by Dynal MPC and cultivated 7-10 days in IMDM (Gibco), with 5% human serum (Gemini Bio-Products), in the presence of 100 IU/ml Interleukin-2 (PeproTech, NJ, USA). The beads were removed from the culture before electroporation.

CD8+ cells were isolated from CD3+ cells by Cd8+ T Cell Isolation Kit II (Miltenyi Biotec, Germany) according to the manufacturer's recommendations. The purity of selected CD8+ cells was 96%.

Reagents: Yeast tRNA and DNA ladders were purchased from Invitrogen, 8-azaadenosine-5'-triphosphate and cordiocipin—from TrfiLink Biotechnologies, polyadenilic acid—from MP Biomedicals.

RNA Synthesis mRNA constructs based on the Pontelina plumata green fluorescent protein ("GFP") sequence of pmaxGFP plasmid (Amaxa Biosystems) were produced in vitro using T7 RNA polymerase (RNAP). Forward primer contained T7 RNA P promoter and anchoring sequence to the proximal part of the GFP expression cassette. Reverse primer with anchoring sequence to distal part of GFP expression cassette contained a stretch of 100 oligo-dT. mRNA synthesis was provided with mMESSAGE mMASHINE® kit (Ambion), using the procedure recommended by the manufacturer. In some cases the product was additionally polyadenylated using the reagent of the same kit. The final product was treated with DNaseI and purified by Ambion MEGAclear kit or by LiCl precipitation.

Transfections

Electroporation was performed using an Amaxa NUCLEOFECTOR™-II (Amaxa Biosystems, Cologne, Germany) in accordance with manufacturer recommendations. Jurkat and B cell lines were transfected using NUCLEOFECTOR™-II solution V and the set of recommended regimes for electroporation. EML cells were transfected using solutions V, T and R and different regimes of electroporation. T lymphocytes were transfected using T cell NUCLEOFECTOR™-II solution and different regimes of electroporation. Alternative methods of nucleic acids delivery were also used: cationic liposome mediated transfection was performed using LIPOFECTIN or LIPOFECTAMIN (Invitrogen). Electroporation was also performed with the ECM 830 (BTX) (Harvard Instruments, Boston, Mass.) or the Gene Pulser II (BioRad, Denver, Colo.), Multiporator (Eppendorf, Hamburg Germany). All procedures were performed as directed by the manufacturers. pmaxGFP plasmid DNA (Amaxa Biosystems) was used as the DNA control. The efficiency of transfection (ET) was determined 18h after transfection by fluorescence activated cell sorting (FACS). In some experiments transfectants were further analyzed each 24h until GFP could not longer be detected. Cell viability was determined by trypan blue dye exclusion.

Flow Cytometry

Flow cytometry was performed using the fluorescent activated cell sorting (FACS®) assay. Flow cytometry was performed on cell subpopulations was performed at the Yale Cancer Center Flow Cytometry Shared Resource, using a FACS® Calibur flow cytometer (Becton-Dickinson, San Jose, Calif.) equipped with 488 nm laser and the standard filter setup. Fluorescence signals were collected on a logarithmic scale. A minimum of ten thousand cells were interrogated for each sample. Analysis of data was performed using FlowJo software (Tree Star, Inc., San Carlos, Calif.). The expression efficiency was calculated as the difference between the geometric mean of fluorescence of the transfectants and control (mock transfected) cells. Mouse anti-human CD4 FITC (anti-CD4 antibody, fluorescein isothiocyanate conjugated), CD8 PE (anti CD8 antibody, phycoerythrin conjugated, CD19PE (anti-CD19, PE conjugated), and CD3 PerCP-Cy5.5 (anti-CD3 antibody, peridinin chlorophyll protein [PerCP]-Cy5.5 conjugated), were purchased from BD Biosciences Pharmingen (San Diego, Calif.), Streptavidin-PerCP (streptavidin, PerCP conjugated)—from BD Immunocytometry Systems (Philadelphia, Pa.), and Biotin-conjugated goat anti-mouse IgG was from Jackson ImmunoResearch Laboratories (West Grove, Pa.). Cells were stained according to the manufacturer's recommendation.

Electrophoresis:

DNA samples were run in 1% agarose in Tris-acetate buffer, 2 v/cm RNA samples were run in 1% agarose in MOPS-formaldehyde buffer, 2 v/cm, using RNA Millenium marker (Invitrogen) as size standard.

Cytotoxicity Assay

The cytotoxic activity of electroporated CD3+CD8+ cells were evaluated by a standard $^{51}$Cr release method. CRL2261 and lymphoblastoid B cells were used as targets. The target B cells, CRL2261 and K562 cells were labeled with 0.25 mCi of $^{51}$Cr-sodium chromate (MP Biomedicals, Inc., Irvine, Calif., USA) for 1 hour, extensively washed and seeded at a density of $10\times104$ in V-bottom 96 well microplates. Transfected CD8+ CD3+ effector (E) cells were suspended in IMDM (Gibco), 10% FBS medium and added to target cells at different E:T ratios. The plates were incubated at 37° C. for 4h, and aliquotes of each sample were harvested for gamma counting in order to assess 51Cr release. Calculations were carried out in triplicate. Specific lysis was calculated as lysis %=

$$\text{Observed release (c.p.m.)} - \text{spontaneous release (c.p.m.)}/\text{Total release (c.p.m.)} - \text{spontaneous release(c.p.m.)} \times 100$$

where c.p.m. is the count/min released by targets incubated with effector cells. Spontaneous release was determined from wells to which 100 µl of complete medium was added instead of effector cells. Total releasable radioactivity was measured after treating the targets with 100 µl of 1% Tritob X100.

Xenograft Tumor Model

On day 0, 6 week-old female NOD/Scid (NOD/LtSz-Prkdc Scid/J) mice (Jackson Laboratory) were injected in the peritoneum with $3\times10^6$ ffluc+ Daudi cells. On days 2 and 3 tumor engraftment was evaluated by biophotonic imaging. Mice with progressively growing tumors were segregated into 3 treatment groups (8 mice per group) receiving additional intraperitoneal (ip) injection of RPMI medium (medium control) (Group 1) or $5\times10^6$ CTLs: mock transfected CTLs (Group 2) or anti-CD19 CIR mRNA transfected CTLs (Group 3).

Biophotonic Tumor Imaging

Anesthetized mice were imaged using Xenogen IVIS 100 system beginning 15 minutes after ip injection of150 ml of a freshly thawed aqueous solution of D-luciferin (Xenogen, Alameda, Calif.). Each animal was serially imaged in an anterior-posterior orientation at the same relative time point after D-luciferin injection. Photons emitted from flLuc Daudi xenografts were quantified using the software program Living Image (Xenogen), and the bioluminescence signal was measured as total photon flux normalized for exposure time and surface area and expressed in units of photons (p) per second per cm2 per steradian (sr). For anatomic localization, a pseudocolor image representing light intensity (blue, least intense; red, most intense) was superimposed over a digital grayscale body-surface reference image.

Statistical Methods to Analyze Biophotonic Data

To measure the differences between mouse treatment groups, we considered evaluating tumor biophotonic signal over time. The signals were normalized for the initial values on day 3 after tumor injection (also the day of first CTLs injection) which was taken as 1 for each mouse. Data obtained for each group were presented as geometrical mean+/−geometrical SD.

The present invention will be further understood by reference to the following non-limiting examples.

Example 1: RNA Transfection in EML Cells

EML cells are a murine cell line that grows in suspension and has the capacity to differentiate into cells of several hematopoietic lineage in vitro. These cells would be of considerable interest for manipulation in vitro, but, unfortunately, they are relatively resistant to standard transfection methods. EML cells were therefore used as a model for exploring various DNA and RNA transfection methods with difficult cells. For convenience of assaying, a DNA plasmid expressing green fluorescent protein (GFP) was used. The following transfection methods were tested: LIPOFECTIN® and LIPOFECTAMIN® lipofection, electroporation using square wave BTX ECM 830 apparatus or BioRad Gene Pulser II, exponential diminishing wave electroporation using Eppendorf Multiporator, and also Amaxa nucleofector. All methods were optimized according to the recommendations of the manufacturers. The Amaxa nucleofection protocol gave the highest efficiency of transfection. The Amaxa procedure was optimized using different combinations of one of three solutions (V, R, and T) and 8 programs of electroporation.

The best result that could be obtained for plasmid DNA transfection was that 12% of the initial cells showing GFP expression, with slightly less than half the initial cells remaining viable after electroporation. Therefore 25% of the surviving cells expressed GFP under these conditions. Further optimization using the programs recommended by the manufacturer was not effective.

The DNA template was designed from the GFP sequence of the pmaxGFP plasmid. To avoid aberrant transcription of PCR-made DNA templates, a T7 promoter and 3' transcription terminator was introduced in the DNA template directly during PCR. The forward PCR primer contained a T7 RNA polymerase promoter and an anchoring sequence from the 5' untranslated region (5'UTR) of the GFP gene. The reverse primer needed a structure that allowed the correct transcriptional termination (FIG. 1, 2A). The PCR product was used for in vitro transcription by T7 RNA polymerase. The mRNA was purified and delivered into mouse EML cells by nucleofection. pmaxGFP plasmid DNA was used as a control.

Effect of the 5' and 3' UTRs on Expression

GFP mRNA with short UTRs: 6 nucleotides upstream of ATG codon and 35 nucleotides downstream of stop codon, was virtually unexpressed. mRNA which included 44 nucleotides upstream of the ATG codon, and 113 nucleotides downstream of the stop codon, were efficiently expressed (Table 2). Table 2. Transfectability of the GFP mRNA constructs

TABLE 2

Transfectability of the GFP mRNA constructs

Coordinates of ends of DNA matrix for mRNA synthesis

| Left end<br>Distance from first<br>GFP codon (b) | Right end<br>Distance from last<br>GFP codon | Transfectability<br>of<br>GFP mRNA |
|---|---|---|
| −6 | +11 | − |
| −6 | +113 | − |
| −44 | +11 | − |
| −44 | +113 | + |
| −44 | +122 | + |

Effect of the 5'-Cap on the mRNA

It is well known that capping highly increases the efficiency of mRNA translation (Cougot et al., *Trends Biochem. Sci.*, 29:436-444 (2004); Pestova et al., *Proc. Natl. Acad. Sci.*, 98:7029-36 (2001)). The standard $m^7G(5')ppp(5')G$ in vitro capping analog can be incorporated in two orientations, therefore only one half of the mRNA product is active. Recently, Ambion and others introduced a new anti-reverse-cap-analog (ARCA) (Stepinski et al., *RNA*, 7:1486-95 (2001)), which lacks one of the 3'OH groups and can be incorporated in mRNA only in the correct orientation.

Figure 2A:
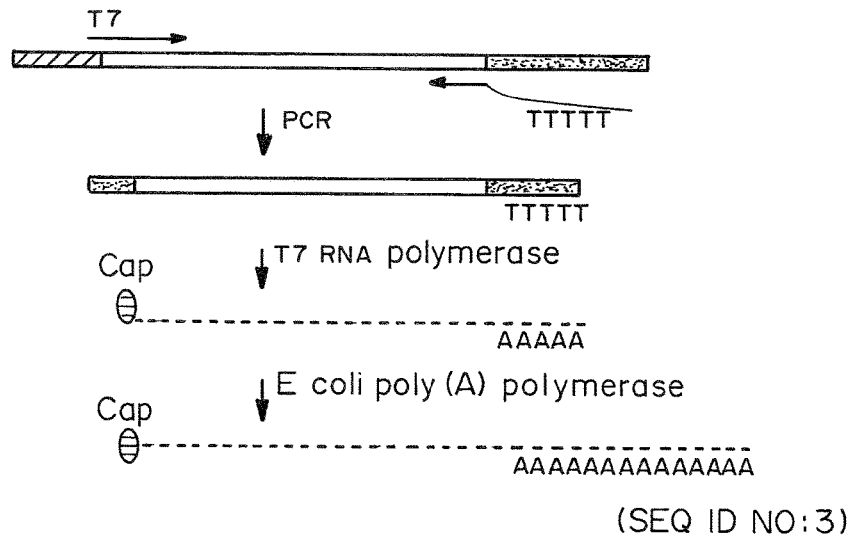
FIG. 2A shows a scheme for mRNA synthesis using a DNA template obtained by PCR with use of specially designed primers. The forward primer contains a bacteriophage promoter suitable for in vitro transcription and the reverse primer contains a polyT stretch. The PCR product is an expression cassette suitable for in vitro transcription. Polyadenylates on the 3' end of the nascent mRNA can prevent aberrant RNA runoff synthesis and creation of double strand RNA product. After completion of transcription polyA tail can be additionally extended with poly(A) polymerase.
Figure 2B:
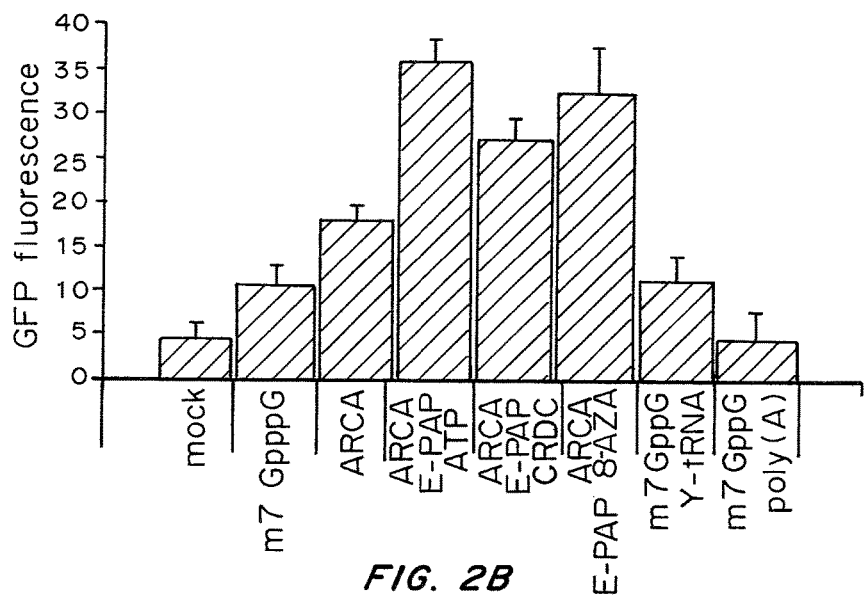
FIG. 2B shows the efficiency of mRNA transfection depending on its structure. EML cells were transfected with 60 µg/ml GFP mRNAs made with a standard cap analog dinucleotide or cap analog, 3'-O-Methyl-m7G[5']ppp[5']G (ARCA). Certain transcripts were treated with $E.$ $coli$ Poly(A) polymerase in the presence of ATP, ATP analogs: cordycepin (CDCP) or 8-aza-adenosine (8-AZA). Certain transfections were performed in the presence of 1 mg/ml polyadenylate RNA or yeast tRNA. GFP expression was analyzed by FACS. The expression efficiency was calculated as the geometric mean of fluorescence intensity (+SD; n=3) as reported by the FACS instrument. Capping as well polyadenylation increased GFP expression. Incorporation of ATP analogs in the 3' end of the mRNA also increased expression, probably by protecting the 3' end from RNAse.

Using ARCA, a two-fold increase of GFP expression compared to the standard capping procedure was obtained, as demonstrated by (FIG. 2B).

Effect of the mRNA 3' Poly (A) Tail Length

There are two basic methods of construction of a poly(A) tail: insertion of a terminal poly(A/T) segment into the DNA template or direct addition of poly(A) residues to the RNA transcripts by a poly(A) polymerase. In these studies, a 3' terminal poly(A/T) stretch introduced by PCR with a reverse primer containing 100 b of poly(T) was sufficient for mRNA expression. However, posttranscriptional RNA polyadenylation by *E. coli* poly(A) polymerase (E-PAP), which expanded the poly(A) tail from 100 up to 300-400 nucleotides, resulted in an additional two-fold increase in expression. The expression could also be increased without tail extension when the ATP in the E-PAP reaction was replaced by modified ATP analogs: cordycepin or 8-azaadenosine (FIG. 2B). The stimulation of expression by poly(A) extension or by the insertion of ATP analogs probably provided better mRNA protection from 3'-exonuclease degradation. GFP expression was not affected by an excess of yeast tRNA, but was inhibited by an excess of free polyadenylate (FIG. 2B).

Figure 3A:
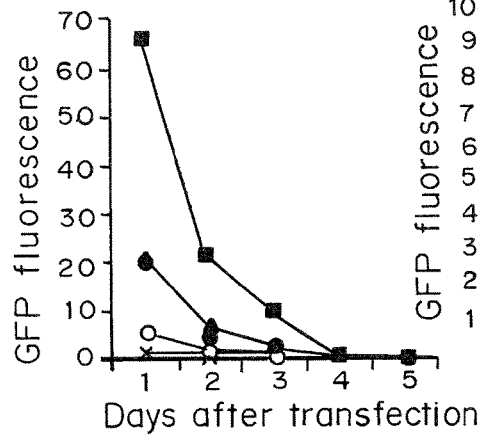
FIGS. 3A-3B show the duration in days of GFP mRNA expression in Jurkat (FIG. 3B) and EML (FIG. 3A) cells. Cells transfected with 6, 17, 50 or 150 mg/ml GFP mRNA or 10 mg/ml DNA were analyzed by FACS during the duration of GFP expression. The expression efficiency was calculated as the difference between the geometric mean of fluorescence of the transfectants and control (mock transfected) cells. The fluorescence value of mock transfected cells was approximately 3 units (negative control). Therefore 63 and 603 units of total fluorescence correspond to 60 and 600 units increase of fluorescence above the control.
Figure 3B:
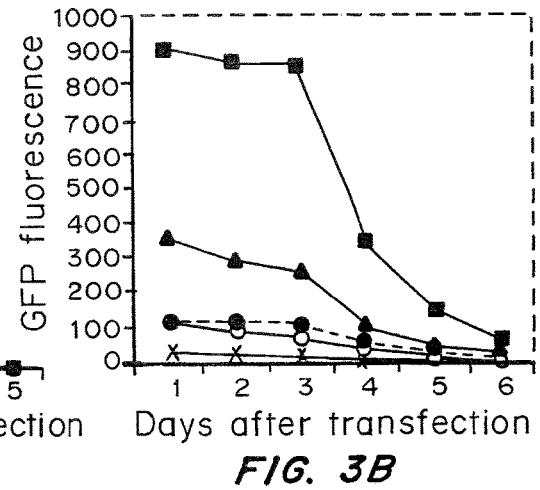

An optimized GFP mRNA construct contained 44b and 113b flanking UTR sequences, an ARCA cap, and a 300-400 b polyadenylate tail. The efficiency of mRNA and DNA transfection had the same pattern of dependence on the electroporation programs used: increasing strength of electroporation resulted in increasing the intensity of GFP expression for DNA and mRNA samples and decreasing of cell viability. Therefore the same nucleofector programs were effective for both DNA and RNA electroporation. After DNA electroporation using the most efficient program-T01, only one fourth of the EML cells were transfected, and these showed highly heterogeneous levels of expression. After mRNA electroporation, almost all cells appeared as a population uniformly expressing GFP. The level of GFP expression caused by plasmid DNA as well as by mRNA in EML cells was highest the day after transfection, and decreased to zero in 4 days (FIG. 3A).

The optimized mRNA construct was used to transfect different human cell lines. Nucleofector programs for each cell line were chosen in accordance with Amaxa cell line protocols. FACS analysis was conducted for EML and Jurkat cells transfected with green fluorescent protein ("GFP") mRNA: 6, 17, 50 and 150 mg mRNA/ml and 10 mg DNA/ml.

In all experiments mRNA transfected almost all of the cells, and resulted in highly efficient and uniform gene expression. Efficiency of transfection measured as the difference between mRNA transfected and mock transfected cell fluorescence.

Table 3: Efficiency of Transfection Measured as the Difference Between mRNA Transfected and Mock Transfected Cell Fluorescence.

TABLE 3

Efficiency of transfection measured as the difference between mRNA transfected and mock transfected cell fluorescence.

| | mRNA (mg/ml) | | | | DNA (mg/ml) |
|---|---|---|---|---|---|
| | 6 | 17 | 50 | 150 | 10 |
| EML | 3.9% | 54.4% | 89.8% | 95% | 27.4% |
| Jurkat | 88.8% | 96.2% | 97.1% | 97.0% | 81.4% |

Human cells can sustain GFP expression caused by plasmid DNA as well as by mRNA for a longer time than mouse EML cells, up to 10 days. Efficiency of transfection for different human cells calculated as the geometric mean fluorescence of the transfected population, showed striking superiority of mRNA expression to that of DNA Relatively long term GFP expression was also observed in the human B cell lines Bjab, BL2 and Palo.

Figure 3C:
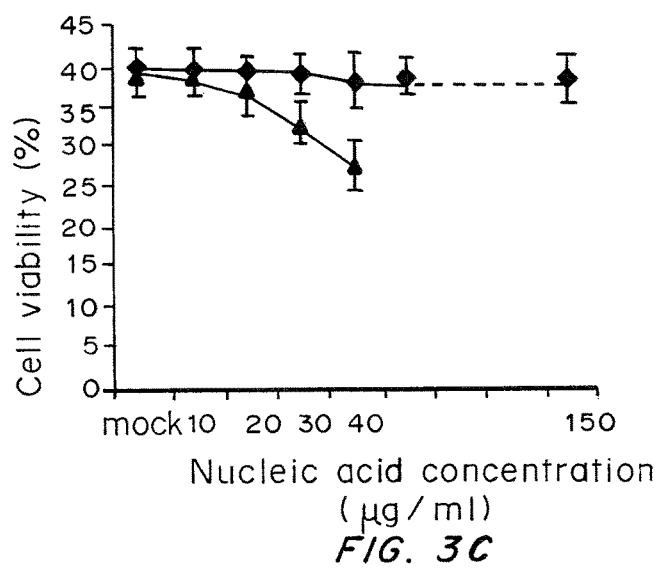
FIG. 3C shows the viability of EML cells transfected with different levels of GFP plasmid DNA (-▲-) or mRNA (-♦-). Viability was calculated by Trypan Blue dye exclusion (Phelach, In: Current protocols in Cell biology, John Wiley & Sons, Inc., 2006). The mean percent (+SD; n=3) of the cells collected 18 h after transfection is shown.

Plasmid DNA was toxic for the cells in a concentration of more than 20 μg/ml. In contrast, no toxicity of GFP mRNA was observed even when it was used at concentrations of more than 150 μg/ml (FIG. 3C).

Example 2. Transfection of Human Primary T Lymphocytes

Figure 4:
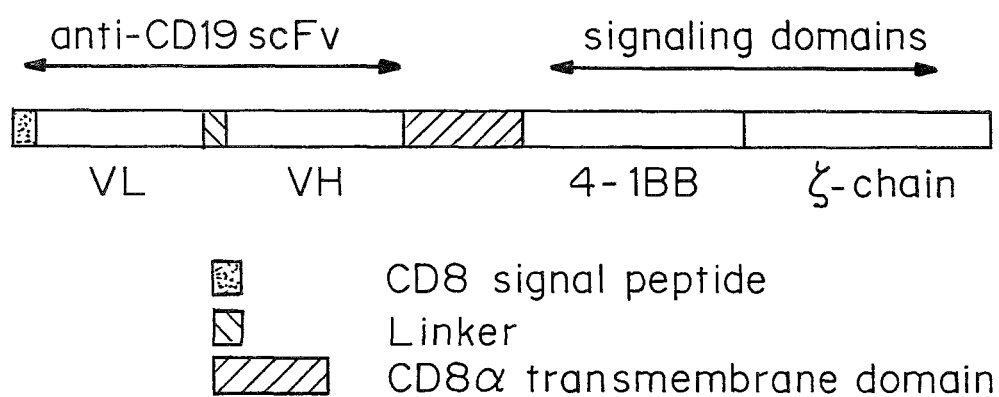
FIG. 4 is a schematic representation of the chimeric anti-CD19-CIR construct. $V_L$ and $V_H$—are extracellular single strand antibody domains, 4-1BB and $\zeta$ are intracellular signal domains.

The method of GFP mRNA synthesis was used to produce the mRNA of the human chimeric anti-CD19 receptor. This receptor contains a leader sequence, an antiCD19 single strand antibody domain, a transmembrane domain and two intracellular signal transduction domains: a 4-1BB and a CD3 zeta, as shown in FIG. 4. Cloned in the appropriate integrative DNA vector, the receptor is able to redirect transfected CD8+ lymphocytes as well as natural killer cells toward the CD19+ targets (Imai at al., *Leukemia*, 18, 676-684 (2004); Imai et al., *Blood*, 106:376-383 (2005). The plasmid pMSCV-IRES-antiCD19-BB-zeta was used as a template to produce the receptor mRNA. The product included the coding sequence, the 50 b 5'UTP, and the 84 b 3'UTP with an extended 400b polyA tail.

Jurkat cells transfected with this mRNA expressed receptor on their surface. Simultaneous transfection of the cells with the receptor and GFP mRNAs showed that both mRNAs can be delivered and expressed without interference. Double mRNA transfection occurred with the same pattern and efficiency as the transfection with single mRNA and was detected in more than 90% of cell population.

Using pmaxGFP plasmid DNA, the transfection procedure for primary human T lymphocytes was optimized. The standard Amaxa Biosystems protocol for activated primary T cells recommends programs T20 and T23. However, these programs resulted in low viability of the cells. The protocol was optimized and better results were obtained with programs T3 and T7, which gave a relatively low but substantial level of pmaxGFP transfection with high viability (greater than 90%). When transfected with receptor mRNA, more than 80% of the CD3+ T lymphocytes expressed the receptor on their surface. Both the CD4+ and the CD8+ subpopulation were equally transfectable and showed the same kinetics of mRNA expression.

Example 3. Transfection of CD3+T Lymphocytes with Anti-CD19-CIR mRNA

Figure 5:
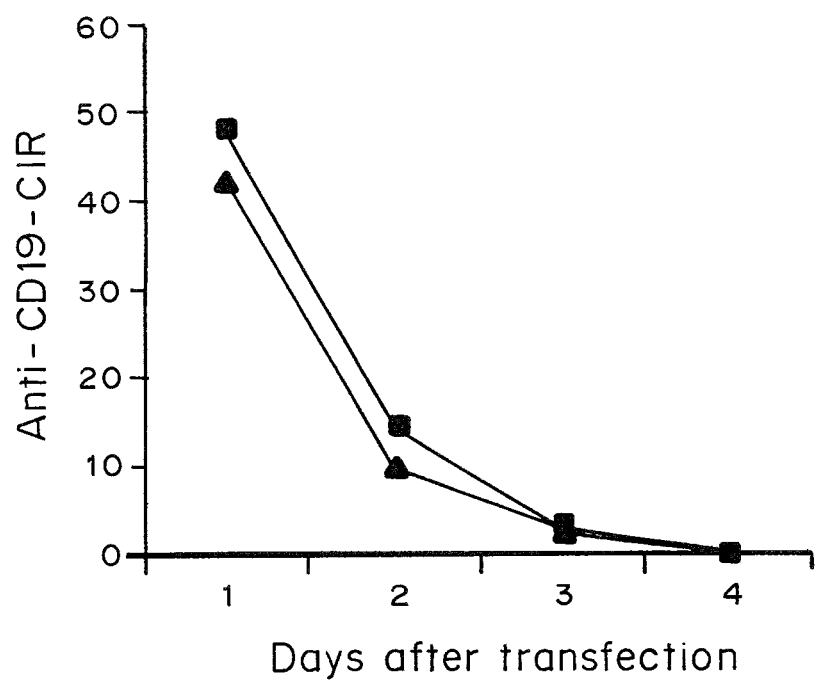
FIG. 5 shows transfection of $CD3^+$ T lymphocytes with anti-CD19-CIR mRNA. $CD4^+$ (-■-) and $CD8^+$ (-▲-) cells were transfected with 40 µg/ml anti-CD19-CIR mRNA and analyzed by FACS during duration (days). Cells were labeled using antibody specific to anti-CD19-CIR, CD8 and CD4. Anti-CD19-CIR expression efficiency was calculated as the difference between the geometric mean of fluorescence of the transfectants and control (mock transfected) cells. The fluorescence value of mock transfected cells was measured as approximately 3 units (negative control). Therefore 63 units of total fluorescence corresponded to 60 units increase of fluorescence above the control.

Cells were transfected with anti-CD19-CIR mRNA (40 μg/ml) and analyzed by FACS. Cells were labeled with antibody specific to anti-CD19-CIR, CD8, and CD4. Anti-CD19-CIR expression efficiency was calculated as the difference between geometric means of fluorescence of the transfectants and control (mock-transfected) cells. The fluorescence value of mock-transfected cells was measured as approximately 3 units (negative control). Therefore 63 units of total fluorescence corresponded to a 60-unit increase in fluorescence relative to the control. Both the CD4+ and CD8+ subpopulations were equally transfectable, possessed the same pattern of mRNA expression, and were able to sustain anti-CD19-CIR expression for at least 3 days (FIG. 5).

Figures 6A, 6B, 6C, 6D:
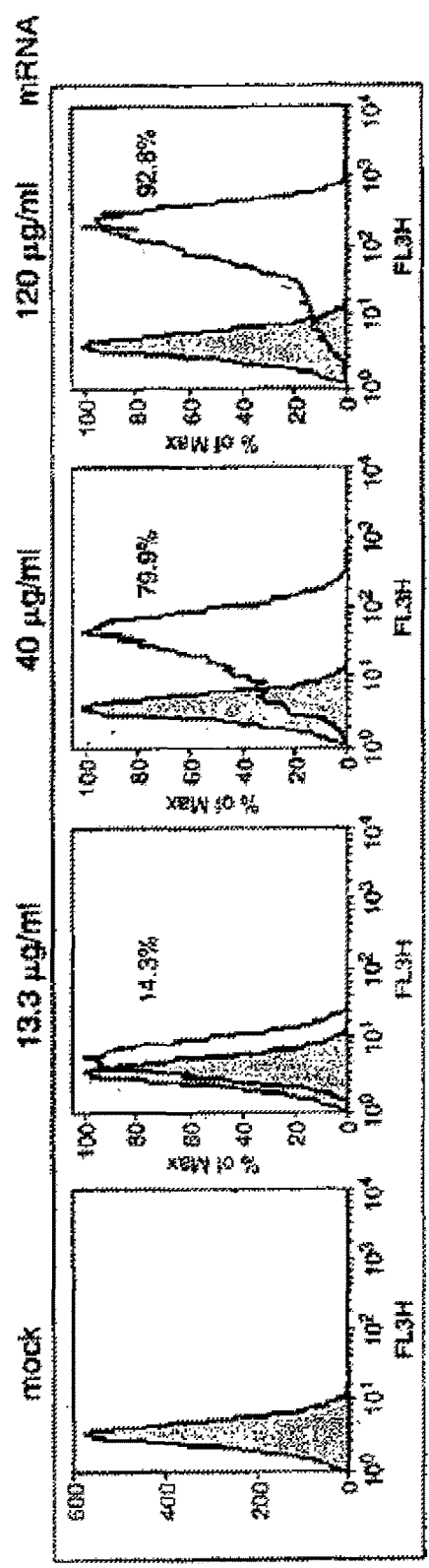
FIGS. 6A-6D are a series of histograms showing FACS analysis of transfectants demonstrating various levels of anti-CD19-CAR expression. Cells were mock transfected (FIG. 6A) or transfected with anti-CD19-CAR mRNA at 13.3 µg/ml (FIG. 6B), 40 µg/ml (FIG. 6C), or 120 µg/ml (FIG. 6D).

Example 4: Cytotoxicity of CD8+ T Lymphocytes Transfected with Various Amounts of Anti-CD19-CIR mRNA FACS analysis of transfectants demonstrating various levels of anti-CD19-CIR expression. CD8+ T lymphocytes (CTLs) were transfected with various amounts of anti-CD19-CIR mRNA. Cells were mock transfected (FIG. 6A) or transfected with anti-CD19-CIR mRNA at 13.3 μg/ml (FIG. 6B), 40 μg/ml (FIG. 6C), or 120 μg/ml (FIG. 6D). The same transfectants were analyzed for cytotoxicity with different targets at the indicated E:T ratio. T lymphocytes were incubated for 4 hr with different target cells, loaded with 51Cr: autologous cells (FIG. 6E); allogeneic CD19+ B lymphoblasts (FIG. 6F); CD19- K562 cells (FIG. 6G).

CD8+ T lymphocytes transfected with anti-CD19-CIR mRNA specifically killed CD19+ targets, whereas mock-transfected control lymphocytes were not cytotoxic. The CD19-negative target cell line K562 was resistant to receptor-mediated killing (FIG. 6G). Of note, even the minimal level of receptor expression detectable by FACS analysis was sufficient for target cell killing (FIGS. 6E and 6F). This result was reproduced with lymphocytes from three different donors.

The experiments above demonstrate that human lymphocytes can be transfected with anti-CD19 CIR mRNAs with high efficiency. After transfection virtually the whole cell populations uniformly expressed chimeric receptors and possessed cytotoxicity against allogeneic and autologous B cells. The expression of the receptor on the surface of lymphocytes was detected for at least 3 days after transfection (FIG. 5). Even the minimal detectable level of receptor expression was sufficient for cytotoxicity. The results in FIG. 5 demonstrate that transfected cytotoxic T lymphocytes (CTLs) can sustain their cytotoxicity for at least several days.

Example 5: Cytotoxicity of CD8+ T Lymphocytes Transfected with Anti-CD19 Chimeric Receptor mRNA Against Different CD19+ Tumor Cells In a $^{51}$Cr assay, it was observed CIR-specific lysis of all CD19+ targets tested, including Daudi lymphoma and NALM6 leukemia cell lines, as well as autologous B lymphoblastoid cells, whereas mock-transfected control lymphocytes were not cytotoxic (FIG. 7B-7D). The CD19-negative target cell line K562 was resistant to receptor-mediated killing (FIG. 7A).

Example 6: Effect of Lymphocyte Activation on mRNA Transfection

The necessity of lymphocyte activation for mRNA transfection was analyzed (FIGS. 8A-8C). Because nucleofector program efficiencies were similar for both DNA and RNA electroporation (US, Amaxa), lymphocyte transfectability was determined using transient transfection with a GFP plasmid DNA. CD3+CD8+ lymphocytes taken without activation were electroporated with GFPmax plasmid DNA using the following different programs recommended by Amaxa for these cells: T7, T13, T20, U1, U8, U10, U5, U14, U9.

The T7 program was chosen for the next step. CD3+CD8+ lymphocytes were incubated 1 or 7 days with CD3-CD28 beads and IL2 and then transfected with anti-CD19 CIR mRNA.

Non-activated CD3+CD8+ cells were virtually untransfectable: less than 2% of the whole population showed green fluorescence determined by expression of GFP transgene. CD3+CD8+ lymphocytes activated by 7 day incubation with CD3-CD28 beads and IL2 showed normal level of transfectability—up to 40% of the cells expressed GFP for programs T13 and T7, with correspondent viability 40 and 55%.

Both samples were transfected using the T7 program with similar efficiency and possessed the same level of cytotoxicity against CD19+ targets. Therefore, CD8+ lymphocyte activation is essential for CIR mRNA transfection and one day of cell incubation with Cd3-CD29 beads and IL2 is sufficient for CTL activation.

The presence of two signaling domains in the cytoplasmic part of CIR facilitates lymphocyte proliferation. However it was not clear if their activity can produce synergistic effects on receptor-mediated cytotoxicity. To investigate this, the 4-1BB signaling part of the anti-CD19 CIR was deleted by a 3-step PCR. This construct was transcribed into mRNA and compared with the original RNA. Both original CIR mRNA and the CIR mRNA construct with 4-1BB deletion transfected CTLs with similar efficiency and generated a similar level of cytotoxicity against CD19+ targets. Thus, in short run experiments where lymphocyte proliferation is not very important, the presence of the zeta subunit as a sole cytoplasmic domain in CIR is sufficient.

Example 7: Modulation Different Types of Lymphocytes with Anti-CD19 CIR mRNA The killing efficiency of NK cells stably transfected with CD19 CIR has been previously demonstrated by Imai, et al., *Leukemia*, 18:676-684 (2004) using retroviral transduction. The ability to transfect NK cells as well as T cells from the same donor with CD19CIR mRNA was tested. Efficiency of electroporation depends on the source of lymphocytes, and electroporation should be optimized for each donor. Also, NK cells electroporation is often less efficient then electroporation of T cells (Amaxa).

Electroporation was optimized using cells obtained from a single donor. CD3+ T cells (CD4+ and CD8+) as well as CD56+ cells (CD3+ CD56+ CIK and CD3− CD56+ NK cells) were transfected with GFP transgene. T7 Amaxa program with a T cell Amaxa kit was efficient for both cell groups and chosen for farther experiments. Three subpopulations: CD3+CD8+, CD3+CD4+ T cells and CD3− CD56+ NK cells were separated, electroporated with anti-CD19 CIR mRNA and tested for cell cytotoxicity toward autologous B cells. The lymphocytes subpopulations: CD8+, CD4+ T cells and a mixture of CD8+ and CD4+ cells (in a 1:1 ratio) as well as NK cells were transfected with anti-CD19 CIR mRNA. Target cells were loaded with $^{51}$Cr and analyzed for cytotoxicity. At the E:T ratios shown in FIGS. 9A-9D, all cell populations expressing the anti-CD19 chimeric receptor were cytotoxic. These studies demonstrate that there is no need to separate any specific type of cytotoxic cells in order to increase the efficiency killing target cells; rather the entire lymphocyte population could be used for mRNA CIR transfection.

Figure 10A:
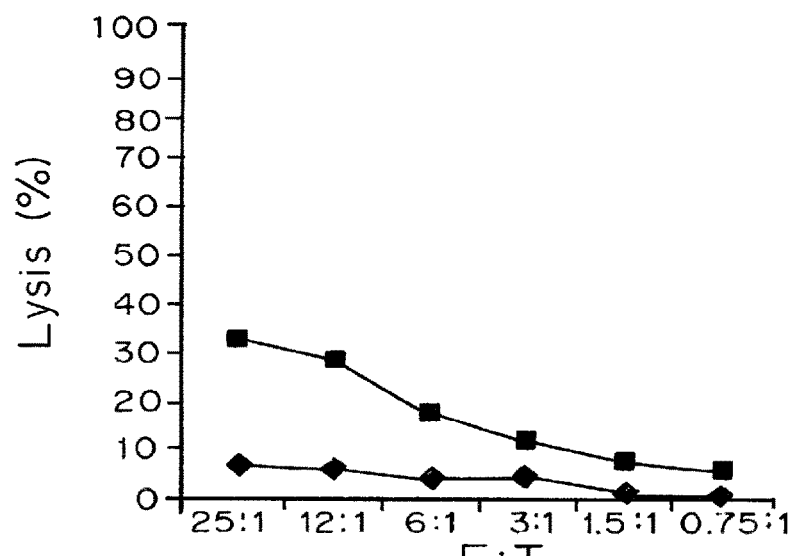
FIGS. 10A and 10B show cytotoxicity of mRNA-modified CTLs against mRNA-modified CD19– tumor cells.
Figure 10B:
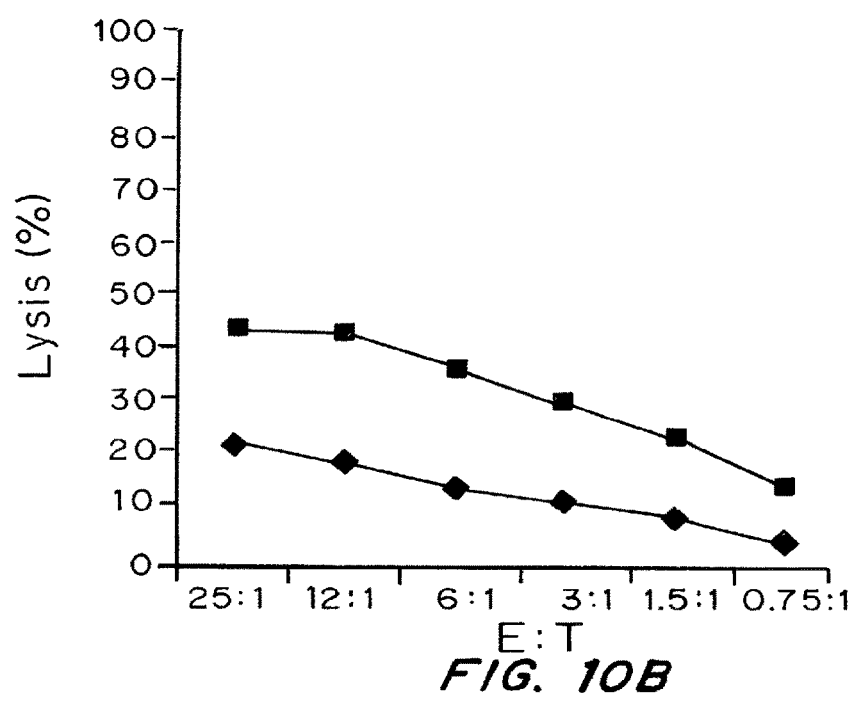
Figure 11:
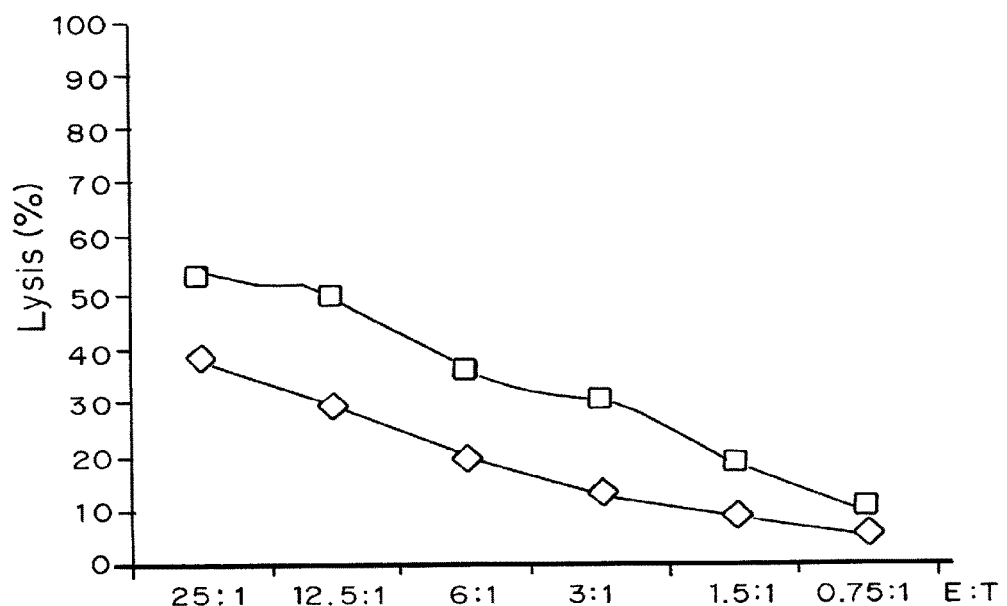
FIG. 11 shows cytotoxicity of mRNA-modified CTLs against mRNA-modified myeloma cells. RPMI8226 myeloma cells that were either mock transfected (-◇-) or transfected with CD19 receptor mRNA (-□-) were loaded with 51Cr, mixed with anti-CD19 CIR+ CTLs and analyzed for cytotoxicity in the presence of anti-MHC1. Expression of CD19 receptor on myeloma cells increased their sensitivity to CIR-mediated killing.

Example 8: Lymphocyte Reprogramming Against K562, Melanoma and Myeloma Cells Solid tumor cells usually do not express CD19. CD9 negative A2058 melanoma and RPMI8126 myeloma cell lines, and also K562 cells, were transfected with CD19 receptor mRNA and used as a targets. The CD19 gene was obtained from ORIGEN, transcribed in vitro and then the mRNA introduced by electroporation in A 2058 and K562 cells. Next day the whole population of target cells uniformly expressed the CD19 (FIG. 10A) and was loaded with $^{51}$Cr and used as target for CD8+ CTLs transfected with anti-CD19 CIR mRNA. Anti-CD19 CIR+ CTLs were able to kill transfected CD19+ melanoma and k562 cells, but possessed low or no cytotoxicity against non-transfected, targets (FIG. 10B). A similar result was obtained with RPMI8126 myeloma cells used as a target (FIG. 11).

Example 9: Lymphocyte Reprogramming Against Solid Tumor Cells Using

8H9 CIR

Figure 12A:
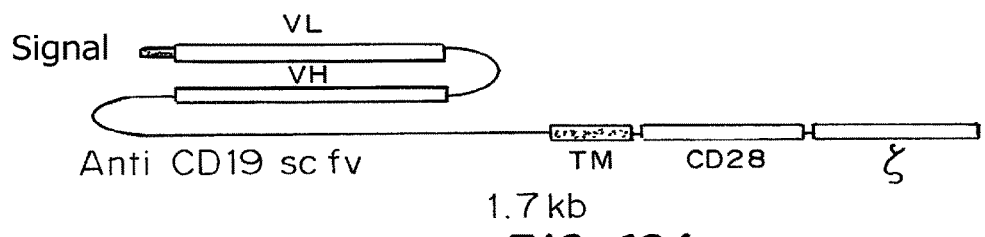
FIG. 12A shows the structure of 8H9 CIR, which can recognize gp58 antigen presented on various solid tumors (Cheung, et al. *Hybridoma and Hybridomics* 22(4):209-218 (2003).

Another chimeric receptor which is made with the 8H9 antibody against a gp58 antigen protein often expressed on different tumor lines (Cheung et al., *Hybridoma and Hybridomics*, 22:209-218 (2003)) (see FIG. 12A) was introduced into human CTLs.

Transfected lymphocytes killed all different solid tumor cells, such as primary melanoma, breast ductal carcinoma, rhabdosarcoma and breast adenacarcinoma which express the correspondent cancer antigen on their surface. Antigen negative K562 cells were resistant to such killing (FIG. 12B-12F).

Example 10: Cytotoxic Activity of Anti-CD19 CIR+ CTLs In Vivo

A xenogenic mice model for lymphocyte therapy of Daudi lymphoma described by Kowolik, et al., *Cancer Res.*, 66(22):10995-1004 (2006) was used. 9 none-obese diabetic/severe combined immunodeficiency (NOD/Scid) mice were divided into 3 groups. Each group was ip injected with either $1\times10^6$, $3\times10^6$ or $9\times10^6$ ffLuck Daudi cells per mouse and analyzed by biophotonic measurements Exponentially growing tumors were established in all mice 3 days after injection. In an initial experiment 6 mice were ip injected with $3\times10^6$ ffLuc+ Daudi cells and 3 days later therapy with human CTLs was initiated. Because the receptor stays on the CTL surface for about 3-4 days, the mice were injected with $5\times10^6$ CTLs per mice every third day. Half of the mice were injected twice on day 3 and day 6 after ffLuck Daudi lymphoma introduction, with mock CTLs (control) and the other half with anti-CD19 CIR mRNA modified CTLs. Treatment with modified cells resulted in marked regression of tumors, while in control group tumors continued to grow.

Figure 13:
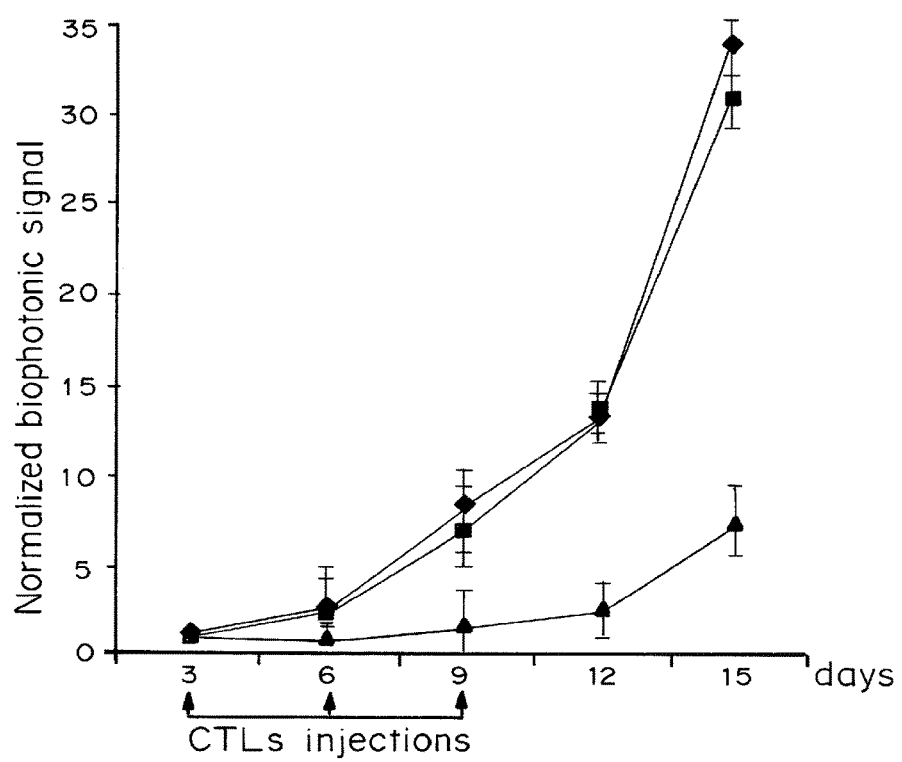
FIG. 13 shows the in vivo activity of anti-CD19 CIR$^+$ CTLs. 21 Nod-SCID mice were injected with $3\times10^6$ luciferase (fflux) expressing Daudi cells and developed exponentially growing tumors on day 3 after injection. These were imaged and divided into 3 groups: treated with RPMI medium (-♦-), mock transfected (-■-) or anti-CD19 CIR transfected (-▲-) CD8$^+$ CTLs. Groups received injections of $5\times10^6$ CTLs on days 3, 6 and 9. Groups received injections of $5\times10^6$ CTLs on days 3, 6 and 9. The mice were imaged on days 3, 6, 9, 12 and 15.

A larger experiment was then performed. $3\times10^6$ ffLuc Daudi cells per mice were seeded into the peritoneum of 24 NOD/Scid mice. 3 days later mice were analyzed by biophotonic measurements and were divided into 3 groups (8 mice per group, with median ffLuc signal (~$6\times10^8$ p/s/cm$^2$/sr), similar for each group. The mice were injected with $5\times10^6$ CTLs per mouse every third day and were given CTLs injections three times on days 3, 6 and 9. The mice were imaged on days 3, 6, 9, 12 and 15. Compared with tumor-bearing control mice given RMPI medium alone (group 1) and mock transfected CTLs (group 2), there was significant reduction of tumor ffLuc signal in mice given anti-CD19 CIR mRNA transfected CTLs (group 3) (FIG. 13).

Pseudocolor image representing light intensity and anatomic localization of the fflluc-Daudi cells in three representative mice and longitudinal monitoring of the bioluminescent signals of ffLuc+ Daudi cells show that tumor growth inhibition was still evident 3 days after the last CTLs injection on day 12. For each group of mice the biophotonic signal outcome was normalized by the initial values at the beginning of CTL-mediated treatment. Geometric means of the signal was used for presentation based on the assumption of the lognormal distribution for the sizes of the tumors (Spratt, I Surgical Research, 9:151-157 (1969)).

Materials and Methods for Examples 11-13

Cells

Neonatal foreskin keratinocytes and nenotal human foreskin fibroblasts were obtained from the Yale Cell Culture Core Facility. Keratinocytes were cultured in serum-free low calcium medium (Epilife, Invitrogen); fibroblasts were cultured in DMEM medium in 10% heat-inactivated fetal bovine serum (Gibco). For reprogramming with mRNA constructs, keratinocytes were electroporated with mRNA transcripts corresponding to reprogramming factors as described below. For initial experiments mRNA corresponding to each of four transcription factors (OCT4, SOX2, KLF4, c-MYC) were used in a 1:1:1:1 ratio respectively. For experiments using high OCT4 concentrations, the same four factors were used in a 3:1:1:1 ratio. For experiments using the initial four factors plus either NANOG or P53DD, the five mRNA transcripts were present in a ratio of 1:1:1:1:1. After viral infection or electroporation, keratinocytes were grown in fresh serum-free, low calcium medium at 37 C and 5% $CO_2$ for 2 days, after which they were trypsinized and seeded onto multi-well plates containing irradiated mouse fibroblasts. Transfected cells were seeded $2.5\times10^6$ cells/cm$^2$ and cultured with ES cell medium (DMEM/F12 containing 20% KOSR (vol/vol), 5-10 ng ml$^{-1}$ bFGF, 1 mM L-Gln, 100 µM nonessential amino acids, 100 M 2-mercaptoethanol, 50 U ml$^{-1}$ penicillin and 50 mg ml$^{-1}$ streptomycin). Neonatal human foreskin fibroblasts were used to confirm the expression of individual mRNA constructs of the various reprogramming factors and were cultured in DMEM with 10% heat inactivated fetal bovine serum. Western blot analysis was used to confirm the expression of individual mRNA constructs of the various reprogramming factors.

PCR

Gene amplification was performed with AccuPrime Pfx DNA polymerase (Invitrogen) according to the manufacturer's protocol. 25 to 30 cycles of PCR were performed in standard 50-µl reaction using 0.1 µg of template DNA. The forward primer contained the T7 RNA promoter and an anchoring sequence in the proximal part of the gene expression cassette. The reverse primer, with anchoring sequence in the distal part of the gene expression cassette, contained a stretch of 100 dT residues. 3-step PCR to delete 4-1BB signaling part of the anti-CD19 CIR was performed by a standard procedure.

RNA Synthesis mRNA constructs based on the Pontelina plumata green fluorescent protein ("GFP") sequence of pmaxGFP plasmid (Amaxa Biosystems) were produced in vitro using T7 RNA polymerase (RNAP). Forward primer contained T7 RNA P promoter and anchoring sequence to the proximal part of the GFP expression cassette. Reverse primer with anchoring sequence to distal part of GFP expression cassette contained a stretch of 100 oligo-dT.

mRNA synthesis was performed with mMESSAGE mMASHINE® kit (Ambion), using the procedure recommended by the manufacturer. One hundred to 200 ng of DNA made by PCR with no further purification was used for the standard 20 µl transcription reaction. The product was treated with *Escherichia coli* poly (A) polymerase (from the same kit) in the presence of 1 mM ATP according to the Ambion polyadenylation protocol. The yield of mRNA was 20 to 60 µg of mRNA per reaction. The final product was treated with DNase I (Ambion) and purified with an Ambion MEGAclear kit or by LiCl precipitation. RNA quality was verified by agarose gel electrophoresis, and RNA was stored at −80° C.

In some cases the product was additionally polyadenylated using the reagent of the same kit. The final product was treated with DNaseI and purified by Ambion MEGAclear kit or by LiCl precipitation.

Transfections

Electroporation was performed using an Amaxa NUCLEOFECTOR™-II (Amaxa Biosystems, Cologne, Germany) in accordance with manufacturer recommendations. All cells were electroporated with use of 30-120 mg/ml mRNA per sample. Cells were used in a concentration of 10-250 million per ml. In this interval of values the efficiency of transfection does not depend on cell density. The efficiency of transfection was determined by FACS 18 hours after transfection. Cell viability was determined by trypan blue exclusion.

Cells were used in a concentration of 10-50 million per ml. In this interval of values the efficiency of transfection does not depend on cell density. The efficiency of transfection was determined by FACS eighteen hours after transfection. Cell viability was determined by trypan blue exclusion.

Cationic-liposomal transfection experiments were carried out using the TransIT®-mRNA Transfection Kit (Minis Bio, WI 53711). Conditions were optimized for keratinocyte and fibroblast transfection according to the manufacturer's recommendations. Transfection of both keratinocytes and fibroblasts was performed in cell culture conditions on a feeder layer of irradiated mouse embryonic fibroblasts.

Flow Cytometry

Flow cytometry was performed using the fluorescent activated cell sorting (FACS®) assay. Flow cytometry was performed on cell subpopulations was performed at the Yale Cancer Center Flow Cytometry Shared Resource, using a FACS® Calibur flow cytometer (Becton-Dickinson, San Jose, Calif.) equipped with 488 nm laser and the standard filter setup. Fluorescence signals were collected on a logarithmic scale. A minimum of ten thousand cells were interrogated for each sample. Analysis of data was performed using FlowJo software (Tree Star, Inc., San Carlos, Calif.). The expression efficiency was calculated as the difference between the geometric mean of fluorescence of the transfectants and control (mock transfected) cells.

Electrophoresis

DNA samples were run in 1% agarose in Tris-acetate buffer, 2 v/cm RNA samples were run in 1% agarose in MOPS-formaldehyde buffer, 2 v/cm, using RNA Millenium marker (Invitrogen) as size standard.

Example 11: mRNA Transfection of Human Fibroblasts

To assess the functionality of mRNA transcripts, transcripts for OCT4, SOX2 (Genbank accession no. NP_003097.1 (protein), NM_003106.2 (mRNA/cDNA)), KLF4 (Genbank: AAH30811.1 (protein), BC030811.1 (mRNA/cDNA)), c-MYC (Genbank: CAA25288.1 (protein), X00676 (mRNA/cDNA)), and NANOG (Genbank: AAP49529.1 (protein), AY230262 (mRNA/cDNA)) were individually transfected into neonatal human foreskin fibroblasts. Protein synthesis was assessed by Western blot analysis. Upon transfection each transcript allowed for significant protein production compared with untransfected control fibroblasts. Sample quantities were standardized by determining pre-lysis cell quantity or by protein quantitation of cell lysates by the bicinchoninic acid (BCA) protein assay.

In all cases protein synthesis was evident above levels of untransfected control samples.

Example 12: mRNA Transfection of Human Keratinocytes

Keratinocytes were transfected with mRNA transcripts coding for reprogramming transcription factors. Initially, keratinocytes were electroporated with OCT4, SOX2, KLF4, and c-MYC mRNA transcripts (day 0). After transfection, cells were grown in keratinocyte medium for 2 days without a feeder cell layer. On day 2, cells were trypsinized and moved to feeder cell layers in multi-well plates with or without 10 mM valproic acid (VPA) supplement.

Transfected keratinocytes began to show evidence of transformation on day 4, at which time small colonies began to form that were particularly abundant in VPA-containing cultures. No colonies were observed in untransfected control cells in either the presence or absence of VPA.

Example 13: siRNA Transfection of Jurkat Cells

Jurkat T cells were electroporated with different amount of FITC labeled siRNA. The condition and the kinetics of siRNA transfection were identical to mRNA transfection. Transfection of Jurkat cells with EGFP mRNA (Clontech) and anti-GFP siRNA (GCAAGCUGACCCUGAAGUUCAU) (SEQ ID NO:4) resulted in 80% inhibition of GFP mRNA expression the day after transfection. No toxicity in siRNA transfection was observed in the interval of 0-15 mkg siRNA/ml.

We claim:

1. An immune cell comprising one or more RNAs prepared by in vitro transcription,
   wherein the one or more RNAs encode one or more polypeptides,
   wherein at least one of the polypeptides is a heterologous polypeptide that renders the immune cell specific for a tumor, virus, bacteria or fungal antigen expressed on the surface of the cells of a subject, and
   wherein the cell is free from DNA encoding the heterologous protein.

2. The cell of claim 1, wherein the one or more RNAs are prepared by in vitro transcription of a linear double stranded DNA template prepared by polymerase chain reaction (PCR).

3. The cell of claim 2, wherein the linear double stranded DNA template comprises:
   an RNA polymerase promoter on the coding strand of the double-stranded DNA,
   a 5' untranslated region less than 3,000 nucleotides in length and effective for translation of the RNA into the heterologous polypeptide after transfection into a eukaryotic cell,
   an open reading frame that encodes the heterologous polypeptide,
   3' untranslated region effective for translation of the RNA into a detectable polypeptide after transfection into a eukaryotic cell, and a poly(A) stretch of 50-5,000 nucleotides on the coding strand of the double-stranded DNA,
   wherein the promoter is heterologous to the open reading frame, and
   wherein the DNA template terminates with the 3' end of the poly(A) stretch.

4. The cell of claim 1, wherein one of the RNAs encodes one or more chimeric antigen receptors (CAR), and wherein the immune cell is contacted with an effective amount of the CAR RNA for the encoded CAR polypeptide or polypeptides to be detected on the surface of the immune cell.

5. The cell of claim 4, wherein the CAR is a CD19 CAR.

6. The cell of claim 5, wherein the CD19 CAR comprises
   (i) an anti-CD19 single strand antibody domain, a transmembrane domain, a 4-1BB domain, and a CD3 zeta domain; or
   (ii) an anti-CD19 single strand antibody domain, a transmembrane domain, and a CD3 zeta domain.

7. The cell of claim 4, further comprising one or more transfected RNAs that renders the cell resistant to one or more inhibitory molecules.

8. The cell of claim 1, wherein the cell is a T cell or Natural Killer (NK) cell.

9. The cell of claim 3, wherein the heterologous polypeptide is selected from the group consisting of a ligand or a receptor of an immune cell, a polypeptide that stimulates or inhibits a function of the immune system, and a polypeptide that inhibits the function of an oncogenic polypeptide.

10. The cell of claim 1, wherein the cell is vector-free.

11. The cell of claim 1, wherein expression of the heterologous polypeptide is transient.

12. The cell of claim 1, wherein expression of the heterologous polypeptide is absent a permanent alteration of the cell's genome.

* * * * *

UNITED STATES PATENT AND TRADEMARK OFFICE
CERTIFICATE OF CORRECTION

PATENT NO. : 10,017,782 B2  
APPLICATION NO. : 15/012285  
DATED : July 10, 2018  
INVENTOR(S) : Peter M. Rabinovich et al.

Page 1 of 1

It is certified that error appears in the above-identified patent and that said Letters Patent is hereby corrected as shown below:

In the Claims

Claim 1, Column 31, Line 27, replace "protein" with --polypeptide--.
Claim 3, Column 31, Line 42, replace "3' untranslated" with --a 3' untranslated--.
Claim 9, Column 32, Line 37, replace "claim 3" with --claim 1--.

Signed and Sealed this
Thirteenth Day of August, 2019

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 8
<212> TYPE: RNA
<213> ORGANISM: Artificial Sequence
<220> FEATURE:
<223> OTHER INFORMATION: Synthetic poly Uridine

<400> SEQUENCE: 1 uuuuuuuu                                                                  8

<210> SEQ ID NO 2
<211> LENGTH: 9
<212> TYPE: RNA
<213> ORGANISM: Artificial Sequence
<220> FEATURE:
<223> OTHER INFORMATION: Synthetic polyadenine

<400> SEQUENCE: 2 aaaaaaaaa                                                                 9

<210> SEQ ID NO 3
<211> LENGTH: 14
<212> TYPE: RNA
<213> ORGANISM: Artificial Sequence
<220> FEATURE:
<223> OTHER INFORMATION: Synthetic poly A tail
```

```
<400> SEQUENCE: 3
aaaaaaaaaa aaaa                                                    14

<210> SEQ ID NO 4
<211> LENGTH: 22
<212> TYPE: RNA
<213> ORGANISM: Artificial Sequence
<220> FEATURE:
<223> OTHER INFORMATION: synthetic polynucleotide

<400> SEQUENCE: 4
gcaagcugac ccugaaguuc au                                           22
```